US011318331B2

(12) United States Patent
Shabtay et al.

(10) Patent No.: US 11,318,331 B2
(45) Date of Patent: May 3, 2022

(54) PULMONARY HYPERTENSION TREATMENT

(71) Applicant: Sonivie Ltd., Rosh HaAyin (IL)

(72) Inventors: Or Shabtay, Kibbutz Farod (IL); Dalit Shav, Glen Rock, NJ (US)

(73) Assignee: Sonivie Ltd., Rosh HaAyin (IL)

( * ) Notice: Subject to any disclaimer, the term of this patent is extended or adjusted under 35 U.S.C. 154(b) by 80 days.

(21) Appl. No.: 16/494,321

(22) PCT Filed: Mar. 20, 2018

(86) PCT No.: PCT/IL2018/050321
§ 371 (c)(1),
(2) Date: Sep. 16, 2019

(87) PCT Pub. No.: WO2018/173052
PCT Pub. Date: Sep. 27, 2018

(65) Prior Publication Data
US 2020/0368244 A1 Nov. 26, 2020

Related U.S. Application Data

(60) Provisional application No. 62/473,532, filed on Mar. 20, 2017, provisional application No. 62/473,545,
(Continued)

(51) Int. Cl.
| | |
|---|---|
| *A61K 31/53* | (2006.01) |
| *A61K 31/343* | (2006.01) |
| *A61K 31/191* | (2006.01) |
| *A61K 31/4965* | (2006.01) |
| *A61K 31/519* | (2006.01) |
| *A61K 31/4985* | (2006.01) |
| *A61K 31/506* | (2006.01) |
| *A61B 18/02* | (2006.01) |
| *A61N 7/00* | (2006.01) |
| *A61B 17/3203* | (2006.01) |
| *A61B 18/06* | (2006.01) |
| *A61B 18/08* | (2006.01) |
| *A61B 18/14* | (2006.01) |
| *A61B 18/24* | (2006.01) |
| *A61N 2/02* | (2006.01) |
| *A61N 2/06* | (2006.01) |
| *A61N 5/10* | (2006.01) |
| *A61N 7/02* | (2006.01) |
| *A61B 18/00* | (2006.01) |
| *A61B 18/12* | (2006.01) |
| *A61B 18/18* | (2006.01) |
| *A61B 5/055* | (2006.01) |
| *A61B 6/03* | (2006.01) |
| *A61B 6/00* | (2006.01) |
| *A61B 17/00* | (2006.01) |

(52) U.S. Cl.
CPC ............ *A61N 7/00* (2013.01); *A61B 17/3203* (2013.01); *A61B 18/0206* (2013.01); *A61B 18/06* (2013.01); *A61B 18/082* (2013.01); *A61B 18/1492* (2013.01); *A61B 18/24* (2013.01); *A61K 31/191* (2013.01); *A61K 31/343* (2013.01); *A61K 31/4965* (2013.01); *A61K 31/4985* (2013.01); *A61K 31/506* (2013.01); *A61K 31/519* (2013.01); *A61K 31/53* (2013.01); *A61N 2/02* (2013.01); *A61N 2/06* (2013.01); *A61N 5/1002* (2013.01); *A61N 7/022* (2013.01); *A61B 5/055* (2013.01); *A61B 6/032* (2013.01); *A61B 6/504* (2013.01); *A61B 2017/00292* (2013.01); *A61B 2018/00369* (2013.01); *A61B 2018/00434* (2013.01); *A61B 2018/0212* (2013.01); *A61B 2018/126* (2013.01); *A61B 2018/1253* (2013.01); *A61B 2018/1807* (2013.01); *A61B 2018/1861* (2013.01); *A61N 2007/003* (2013.01); *A61N 2007/0043* (2013.01); *A61N 2007/0078* (2013.01)

(58) Field of Classification Search
None
See application file for complete search history.

(56) References Cited

U.S. PATENT DOCUMENTS

| | | |
|---|---|---|
| 4,319,580 A | 3/1982 | Colley et al. |
| 5,038,789 A | 8/1991 | Frazin |
| (Continued) | | |

FOREIGN PATENT DOCUMENTS

| | | |
|---|---|---|
| CA | 2954897 | 11/2016 |
| CN | 1279595 | 1/2001 |
| (Continued) | | |

OTHER PUBLICATIONS

Advisory Action Before the Filing of An Appeal Brief dated Feb. 4, 2019 From the US Patent and Trademark Office Re. U.S. Appl. No. 14/190,113. (6 pages).

(Continued)

*Primary Examiner* — Kristin A Vajda

(57) ABSTRACT

Disclosed herein is a therapeutically active agent usable in the treatment of pulmonary arterial hypertension (PAH), for use in the treatment of pulmonary arterial hypertension, as well as methods of treating PAH, said treatment and methods comprising administering such an active agent and effecting pulmonary artery denervation in the subject. In some aspects, a sub-therapeutically effective amount of the active agent is administered. In some aspects, the method is devoid of administering such an active agent for at least one month subsequent to the denervation. Further disclosed is a method of treating PAH comprising determining a responsiveness of the subject to at least one therapeutically active agent usable in treating PAH; and effecting pulmonary artery denervation in a subject responsive to the active agent(s).

14 Claims, 8 Drawing Sheets

Related U.S. Application Data filed on Mar. 20, 2017, provisional application No. 62/473,512, filed on Mar. 20, 2017.

(56) References Cited

U.S. PATENT DOCUMENTS

| | | |
|---|---|---|
| 5,226,847 A | 7/1993 | Thomas, III et al. |
| 5,421,338 A | 6/1995 | Crowley et al. |
| 5,467,251 A | 11/1995 | Katchmar |
| 5,471,988 A | 12/1995 | Fujio et al. |
| 5,524,630 A | 6/1996 | Crowley |
| 5,590,653 A | 1/1997 | Aida et al. |
| 5,620,417 A | 4/1997 | Jang et al. |
| 5,620,479 A | 4/1997 | Diederich |
| 5,657,760 A | 8/1997 | Ying et al. |
| 5,699,804 A | 12/1997 | Rattner |
| 5,707,367 A | 1/1998 | Nilsson |
| 5,735,280 A | 4/1998 | Sherman et al. |
| 5,762,066 A | 6/1998 | Law et al. |
| 5,772,642 A | 6/1998 | Ciamacco, Jr. et al. |
| 5,895,355 A | 4/1999 | Schaer |
| 5,895,356 A | 4/1999 | Andrus et al. |
| 5,971,949 A | 10/1999 | Levin et al. |
| 6,007,499 A | 12/1999 | Martin et al. |
| 6,042,556 A | 3/2000 | Beach et al. |
| 6,073,048 A | 6/2000 | Kieval et al. |
| 6,077,225 A | 6/2000 | Brock-Fisher |
| 6,117,101 A | 9/2000 | Diederich et al. |
| 6,119,041 A | 9/2000 | Pomeranz et al. |
| 6,165,127 A | 12/2000 | Crowley |
| 6,210,393 B1 | 4/2001 | Brisken |
| 6,216,041 B1 | 4/2001 | Tierney et al. |
| 6,235,024 B1 | 5/2001 | Tu |
| 6,261,233 B1 | 7/2001 | Kantorovich |
| 6,296,619 B1 | 10/2001 | Brisken et al. |
| 6,379,320 B1 | 4/2002 | Lafon et al. |
| 6,428,477 B1 | 8/2002 | Mason |
| 6,451,013 B1 | 9/2002 | Bays et al. |
| 6,500,121 B1 | 12/2002 | Slayton et al. |
| 6,511,428 B1 | 1/2003 | Azuma et al. |
| 6,511,436 B1 | 1/2003 | Asmar |
| 6,514,249 B1 | 2/2003 | Maguire et al. |
| 6,524,271 B2 | 2/2003 | Brisken et al. |
| 6,527,759 B1 | 3/2003 | Tachibana et al. |
| 6,547,788 B1 | 4/2003 | Maguire et al. |
| 6,599,288 B2 | 7/2003 | Maguire et al. |
| 6,607,502 B1 | 8/2003 | Maguire et al. |
| 6,645,147 B1 | 11/2003 | Jackson et al. |
| 6,740,040 B1 | 5/2004 | Mandrusov et al. |
| 6,752,805 B2 | 6/2004 | Maguire et al. |
| 6,953,460 B2 | 10/2005 | Maguire et al. |
| 6,955,173 B2 | 10/2005 | Lesh |
| 6,978,174 B2 | 12/2005 | Gelfand et al. |
| 7,001,336 B2 | 2/2006 | Mandrusov et al. |
| 7,037,271 B2 | 5/2006 | Crowley |
| 7,084,004 B2 | 8/2006 | Vaiyapttri et al. |
| 7,156,816 B2 | 1/2007 | Schwartz et al. |
| 7,162,303 B2 | 1/2007 | Levin et al. |
| 7,166,098 B1 | 1/2007 | Steward et al. |
| 7,220,233 B2 | 5/2007 | Nita et al. |
| 7,220,258 B2 | 5/2007 | Myhr |
| 7,220,261 B2 | 5/2007 | Truckai et al. |
| 7,285,116 B2 | 10/2007 | De la Rama et al. |
| 7,326,201 B2 | 2/2008 | Fjield et al. |
| 7,341,583 B2 | 3/2008 | Shiono et al. |
| 7,344,529 B2 | 3/2008 | Torchia et al. |
| 7,347,859 B2 | 3/2008 | Garabedian et al. |
| 7,410,486 B2 | 8/2008 | Fuimaono et al. |
| 7,460,369 B1 | 12/2008 | Blish, II |
| 7,470,241 B2 | 12/2008 | Weng et al. |
| 7,479,106 B2 | 1/2009 | Banik et al. |
| 7,510,536 B2 | 3/2009 | Foley et al. |
| 7,538,425 B2 | 5/2009 | Myers et al. |
| RE40,815 E | 6/2009 | Kudaravalli et al. |
| 7,540,846 B2 | 6/2009 | Harhen et al. |
| 7,540,870 B2 | 6/2009 | Babaev |
| 7,563,260 B2 | 7/2009 | Whitmore et al. |
| 7,617,005 B2 | 11/2009 | Demarais et al. |
| 7,620,451 B2 | 11/2009 | Demarais et al. |
| 7,621,929 B2 | 11/2009 | Nita et al. |
| 7,647,115 B2 | 1/2010 | Levin et al. |
| 7,653,438 B2 | 1/2010 | Deem et al. |
| 7,655,005 B2 | 2/2010 | Bhola |
| 7,678,104 B2 | 3/2010 | Keidar |
| 7,704,212 B2 | 4/2010 | Wekell et al. |
| 7,713,210 B2 | 5/2010 | Byrd et al. |
| 7,717,948 B2 | 5/2010 | Demarais et al. |
| 7,727,228 B2 | 6/2010 | Abboud et al. |
| 7,736,317 B2 | 6/2010 | Stephens et al. |
| 7,756,583 B2 | 7/2010 | Demarais et al. |
| 7,762,954 B2 | 7/2010 | Nix et al. |
| 7,771,372 B2 | 8/2010 | Wilson |
| 7,819,868 B2 | 10/2010 | Cao et al. |
| 7,824,348 B2 | 11/2010 | Barthe et al. |
| 7,850,683 B2 | 12/2010 | Elkins et al. |
| 7,850,685 B2 | 12/2010 | Kunis et al. |
| 7,853,333 B2 | 12/2010 | Demarais |
| 7,854,733 B2 | 12/2010 | Govari |
| 7,883,506 B2 | 2/2011 | McIntyre et al. |
| 7,940,969 B2 | 5/2011 | Nair et al. |
| 8,216,216 B2 | 7/2012 | Warnking et al. |
| 8,221,402 B2 | 7/2012 | Francischelli et al. |
| 8,401,667 B2 | 3/2013 | Gustus et al. |
| 8,419,729 B2 | 4/2013 | Ibrahim et al. |
| 8,540,662 B2 | 9/2013 | Stehr et al. |
| 8,568,403 B2 | 10/2013 | Soltesz et al. |
| 8,585,695 B2 | 11/2013 | Shih |
| 8,974,446 B2 | 3/2015 | Nguyen et al. |
| 10,368,893 B2 | 4/2019 | Sverdlik et al. |
| 2001/0007940 A1 | 7/2001 | Tu et al. |
| 2001/0014780 A1 | 8/2001 | Martin et al. |
| 2001/0053885 A1 | 12/2001 | Gielen et al. |
| 2002/0002371 A1 | 1/2002 | Acker et al. |
| 2002/0016624 A1 | 2/2002 | Patterson et al. |
| 2002/0019627 A1 | 2/2002 | Maguire et al. |
| 2002/0022833 A1 | 2/2002 | Maguire et al. |
| 2002/0026127 A1 | 2/2002 | Balbierz et al. |
| 2002/0048310 A1 | 4/2002 | Heuser |
| 2002/0055754 A1 | 5/2002 | Ranucci et al. |
| 2002/0065512 A1 | 5/2002 | Fjield et al. |
| 2002/0077643 A1 | 6/2002 | Rabiner et al. |
| 2002/0169394 A1 | 11/2002 | Eppstein et al. |
| 2002/0188218 A1 | 12/2002 | Lipman |
| 2003/0013968 A1 | 1/2003 | Fjield et al. |
| 2003/0092667 A1 | 5/2003 | Tachibana et al. |
| 2003/0125726 A1 | 7/2003 | Maguire et al. |
| 2003/0151417 A1 | 8/2003 | Koen |
| 2003/0163190 A1 | 8/2003 | LaFont et al. |
| 2003/0181901 A1 | 9/2003 | Maguire et al. |
| 2003/0195496 A1 | 10/2003 | Maguire et al. |
| 2003/0199747 A1 | 10/2003 | Michlitsch et al. |
| 2003/0199768 A1 | 10/2003 | Cespededs et al. |
| 2004/0006333 A1 | 1/2004 | Arnold et al. |
| 2004/0019687 A1 | 1/2004 | Ozawa et al. |
| 2004/0073660 A1 | 4/2004 | Toomey |
| 2004/0082859 A1 | 4/2004 | Schaer |
| 2004/0102361 A1* | 5/2004 | Bodin .................. A61K 45/06 514/513 |
| 2004/0102769 A1 | 5/2004 | Schwartz et al. |
| 2005/0015079 A1 | 1/2005 | Keider |
| 2005/0020967 A1 | 1/2005 | Ono |
| 2005/0096542 A1 | 5/2005 | Weng et al. |
| 2005/0096647 A1 | 5/2005 | Steinke et al. |
| 2005/0215946 A1 | 9/2005 | Hansmann et al. |
| 2005/0240170 A1 | 10/2005 | Zhang et al. |
| 2005/0288730 A1 | 12/2005 | Deem et al. |
| 2006/0009753 A1 | 1/2006 | Fjield et al. |
| 2006/0052774 A1 | 3/2006 | Garrison et al. |
| 2006/0058711 A1 | 3/2006 | Harhen et al. |
| 2006/0079816 A1 | 4/2006 | Barthe et al. |
| 2006/0084966 A1 | 4/2006 | Maguire et al. |
| 2006/0173387 A1 | 8/2006 | Hansmann et al. |
| 2006/0229594 A1 | 10/2006 | Francischelli et al. |
| 2006/0241442 A1 | 10/2006 | Barthe et al. |
| 2006/0241739 A1 | 10/2006 | Besselink et al. |

(56) References Cited

U.S. PATENT DOCUMENTS

| | | |
|---|---|---|
| 2006/0264809 A1 | 11/2006 | Hansmann et al. |
| 2007/0043297 A1 | 2/2007 | Miyazawa |
| 2007/0088346 A1 | 4/2007 | Mirizzi et al. |
| 2007/0142831 A1 | 6/2007 | Shadduck |
| 2007/0142879 A1 | 6/2007 | Greenberg et al. |
| 2007/0167824 A1 | 7/2007 | Lee et al. |
| 2007/0203479 A1 | 8/2007 | Auth et al. |
| 2007/0222339 A1 | 9/2007 | Lukacs et al. |
| 2007/0225619 A1 | 9/2007 | Rabiner et al. |
| 2007/0233057 A1 | 10/2007 | Konishi |
| 2007/0249997 A1 | 10/2007 | Goodson, IV et al. |
| 2007/0282407 A1 | 12/2007 | Demarais et al. |
| 2008/0039745 A1 | 2/2008 | Babaev |
| 2008/0077202 A1 | 3/2008 | Levinson |
| 2008/0086073 A1 | 4/2008 | McDaniel |
| 2008/0114354 A1 | 5/2008 | Whayne et al. |
| 2008/0125829 A1 | 5/2008 | Velasco et al. |
| 2008/0139971 A1 | 6/2008 | Lockhart |
| 2008/0146924 A1 | 6/2008 | Smith et al. |
| 2008/0171934 A1 | 7/2008 | Greenan et al. |
| 2008/0179736 A1 | 7/2008 | Hartwell et al. |
| 2008/0183110 A1 | 7/2008 | Davenport et al. |
| 2008/0195000 A1 | 8/2008 | Spooner et al. |
| 2008/0214966 A1 | 9/2008 | Slayton et al. |
| 2008/0215039 A1 | 9/2008 | Slatkine et al. |
| 2008/0228111 A1 | 9/2008 | Nita |
| 2008/0249518 A1 | 10/2008 | Warnking et al. |
| 2008/0281297 A1 | 11/2008 | Pesach et al. |
| 2008/0300571 A1 | 12/2008 | LePivert |
| 2008/0300655 A1 | 12/2008 | Cholette |
| 2008/0312643 A1 | 12/2008 | Kania et al. |
| 2009/0018446 A1 | 1/2009 | Medan et al. |
| 2009/0036914 A1 | 2/2009 | Houser |
| 2009/0093737 A1 | 4/2009 | Chomas et al. |
| 2009/0131930 A1 | 5/2009 | Gelbart et al. |
| 2009/0149782 A1 | 6/2009 | Cohen et al. |
| 2009/0163807 A1 | 6/2009 | Sliwa |
| 2009/0216246 A1 | 8/2009 | Nita et al. |
| 2009/0221939 A1 | 9/2009 | Demarais et al. |
| 2009/0221955 A1 | 9/2009 | Babaev |
| 2009/0254078 A1 | 10/2009 | Just et al. |
| 2009/0281478 A1 | 11/2009 | Duke |
| 2009/0299360 A1 | 12/2009 | Ormsby |
| 2010/0036293 A1 | 2/2010 | Isola et al. |
| 2010/0081933 A1 | 4/2010 | Sverdlik et al. |
| 2010/0091112 A1 | 4/2010 | Veeser et al. |
| 2010/0114082 A1 | 5/2010 | Sharma |
| 2010/0125198 A1 | 5/2010 | Thapliyal et al. |
| 2010/0130892 A1 | 5/2010 | Warnking |
| 2010/0137860 A1 | 6/2010 | Demarais et al. |
| 2010/0152625 A1 | 6/2010 | Milo |
| 2010/0168624 A1 | 7/2010 | Sliwa |
| 2010/0168649 A1 | 7/2010 | Schwartz et al. |
| 2010/0191112 A1 | 7/2010 | Demarais et al. |
| 2010/0198040 A1 | 8/2010 | Friedman et al. |
| 2010/0210946 A1 | 8/2010 | Harada et al. |
| 2010/0222851 A1 | 9/2010 | Deem et al. |
| 2010/0228162 A1 | 9/2010 | Sliwa et al. |
| 2010/0262014 A1 | 10/2010 | Huang |
| 2010/0331686 A1 | 12/2010 | Hossack et al. |
| 2010/0331950 A1 | 12/2010 | Strommer |
| 2011/0009779 A1 | 1/2011 | Romano et al. |
| 2011/0028962 A1 | 2/2011 | Werneth et al. |
| 2011/0034809 A1 | 2/2011 | Eberle et al. |
| 2011/0066217 A1 | 3/2011 | Diller et al. |
| 2011/0092781 A1 | 4/2011 | Gertner |
| 2011/0092880 A1 | 4/2011 | Gertner |
| 2011/0106132 A1 | 5/2011 | Barbut et al. |
| 2011/0112400 A1 | 5/2011 | Emery et al. |
| 2011/0178441 A1 | 7/2011 | Tyler |
| 2011/0201973 A1 | 8/2011 | Stephens et al. |
| 2011/0257563 A1 | 10/2011 | Thapliyal et al. |
| 2011/0264086 A1 | 10/2011 | Ingle |
| 2011/0270247 A1 | 11/2011 | Sherman |
| 2011/0282203 A1 | 11/2011 | Tsoref et al. |
| 2011/0282249 A1 | 11/2011 | Tsoref et al. |
| 2011/0319765 A1 | 12/2011 | Gertner et al. |
| 2012/0016273 A1 | 1/2012 | Diederich |
| 2012/0053577 A1 | 3/2012 | Lee et al. |
| 2012/0065494 A1 | 3/2012 | Gertner et al. |
| 2012/0095335 A1 | 4/2012 | Sverdlik et al. |
| 2012/0095371 A1 | 4/2012 | Sverdlik et al. |
| 2012/0095372 A1 | 4/2012 | Sverdlik et al. |
| 2012/0123243 A1 | 5/2012 | Hastings |
| 2012/0123270 A1 | 5/2012 | Klee et al. |
| 2012/0209116 A1 | 8/2012 | Hossack et al. |
| 2012/0215106 A1 | 8/2012 | Sverdlik et al. |
| 2012/0232409 A1 | 9/2012 | Stahmann et al. |
| 2012/0232436 A1 | 9/2012 | Warnking |
| 2012/0265227 A1 | 10/2012 | Sverdlik et al. |
| 2012/0268886 A1 | 10/2012 | Leontiev et al. |
| 2012/0283605 A1 | 11/2012 | Lewis, Jr. |
| 2012/0310233 A1 | 12/2012 | Dimmer et al. |
| 2012/0316559 A1 | 12/2012 | Mayse et al. |
| 2013/0072928 A1 | 3/2013 | Schaer |
| 2013/0131668 A1 | 5/2013 | Schaer |
| 2013/0197555 A1 | 8/2013 | Schaer |
| 2013/0204068 A1 | 8/2013 | Gnanashanmugam et al. |
| 2013/0204167 A1 | 8/2013 | Sverdlik et al. |
| 2013/0204242 A1 | 8/2013 | Sverdlik et al. |
| 2013/0207519 A1 | 8/2013 | Chaggares et al. |
| 2013/0211292 A1 | 8/2013 | Sverdlik et al. |
| 2013/0211396 A1 | 8/2013 | Sverdlik et al. |
| 2013/0211437 A1 | 8/2013 | Sverdlik et al. |
| 2013/0218054 A1 | 8/2013 | Sverdlik et al. |
| 2013/0218068 A1 | 8/2013 | Sverdlik et al. ........... A61K 31/506 |
| 2013/0225595 A1* | 8/2013 | Gillies ................. A61K 31/506 514/250 |
| 2013/0226040 A1 | 8/2013 | Michael et al. |
| 2013/0267875 A1 | 10/2013 | Thapliyal et al. |
| 2013/0296836 A1 | 11/2013 | Barbut et al. |
| 2013/0310822 A1 | 11/2013 | Mayse et al. |
| 2014/0005706 A1 | 1/2014 | Gelfand et al. |
| 2014/0012133 A1 | 1/2014 | Sverdlik et al. |
| 2014/0024975 A1 | 1/2014 | Little et al. |
| 2014/0039286 A1 | 2/2014 | Hoffer |
| 2014/0039477 A1 | 2/2014 | Sverdlik et al. |
| 2014/0074076 A1 | 3/2014 | Gertner |
| 2014/0088585 A1 | 3/2014 | Hill et al. |
| 2014/0163540 A1 | 6/2014 | Iyer et al. |
| 2014/0163652 A1 | 6/2014 | Witzel et al. |
| 2014/0180197 A1 | 6/2014 | Sverdlik et al. |
| 2014/0180277 A1 | 6/2014 | Chen |
| 2014/0194866 A1 | 7/2014 | Wang |
| 2014/0257262 A1 | 9/2014 | Carpentier et al. |
| 2014/0276135 A1 | 9/2014 | Agah et al. |
| 2014/0359111 A1 | 12/2014 | Hilmo et al. |
| 2015/0057599 A1 | 2/2015 | Chen |
| 2015/0073400 A1 | 3/2015 | Sverdlik et al. |
| 2015/0112234 A1 | 4/2015 | McCaffrey et al. |
| 2015/0272668 A1 | 10/2015 | Chen |
| 2016/0059044 A1 | 3/2016 | Gertner |
| 2016/0113699 A1 | 4/2016 | Sverdlik et al. |
| 2016/0374710 A1 | 12/2016 | Sinelnikov et al. |
| 2017/0027645 A1 | 2/2017 | Ben Oren et al. |
| 2018/0326227 A1 | 11/2018 | Sverdlik et al. |
| 2019/0290350 A1 | 9/2019 | Sverdlik et al. |
| 2019/0308003 A1 | 10/2019 | Sverdlik et al. |
| 2019/0366130 A1 | 12/2019 | Sverdlik et al. |
| 2020/0238107 A1 | 7/2020 | Shabtay et al. |
| 2021/0178194 A1 | 6/2021 | Sverdlik et al. |

FOREIGN PATENT DOCUMENTS

| | | |
|---|---|---|
| CN | 101610735 | 12/2009 |
| CN | 101820820 | 9/2010 |
| EP | 1384445 | 1/2004 |
| EP | 1424100 | 6/2004 |
| EP | 1799302 | 3/2006 |
| EP | 1769759 | 4/2007 |
| EP | 1802370 | 7/2007 |
| EP | 2092957 | 8/2009 |
| EP | 2218479 | 8/2010 |
| EP | 2455133 | 5/2012 |

(56) References Cited

FOREIGN PATENT DOCUMENTS

| JP | 07-227394 | 8/1995 | |
|---|---|---|---|
| JP | 09-122139 | 5/1997 | |
| JP | 10-248854 | 9/1998 | |
| JP | 2008-536562 | 9/2008 | |
| JP | 2010-517695 | 5/2010 | |
| WO | WO 91/10405 | 7/1991 | |
| WO | WO 99/16366 | 4/1999 | |
| WO | WO 00/67648 | 10/2000 | |
| WO | WO 01/45550 | 6/2001 | |
| WO | WO 02/096501 | 12/2002 | |
| WO | WO 2004/054448 | 7/2004 | |
| WO | WO 2006/022790 | 3/2006 | |
| WO | WO 2006/041847 | 4/2006 | |
| WO | WO 2006/041881 | 4/2006 | |
| WO | WO 2006/042163 | 4/2006 | |
| WO | WO 2007/001981 | 1/2007 | |
| WO | WO 2007/078997 | 7/2007 | |
| WO | WO 2007/115307 | 10/2007 | |
| WO | WO 2007/127176 | 11/2007 | |
| WO | WO 2008/003058 | 1/2008 | |
| WO | WO 2008/098101 | 8/2008 | |
| WO | WO 2008/102363 | 8/2008 | |
| WO | WO 2010/009473 | 1/2010 | |
| WO | WO 2010/118307 | 10/2010 | |
| WO | WO 2011/053757 | 5/2011 | |
| WO | WO 2011/060200 | 5/2011 | |
| WO | WO 2012/052920 | 4/2012 | |
| WO | WO 2012/052921 | 4/2012 | |
| WO | WO 2012/052922 | 4/2012 | |
| WO | WO 2012/052924 | 4/2012 | |
| WO | WO 2012/052925 | 4/2012 | |
| WO | WO 2012/052926 | 4/2012 | |
| WO | WO 2012/052927 | 4/2012 | |
| WO | WO 2012/061713 | 5/2012 | |
| WO | WO 2013/030743 | 3/2013 | |
| WO | WO 2013/111136 | 8/2013 | |
| WO | WO 2013/134479 | 9/2013 | |
| WO | WO 2013/157009 | 10/2013 | |
| WO | WO 2013/157011 | 10/2013 | |
| WO | WO 2013/162694 | 10/2013 | |
| WO | WO 2014/141052 | 9/2014 | |
| WO | WO 2014/188430 | 11/2014 | |
| WO | WO 2016/084081 | 6/2016 | |
| WO | WO-2016084081 A2 * | 6/2016 | ............... A61N 7/00 |
| WO | WO 2016/084081 A8 | 6/2017 | |
| WO | WO 2018/173052 | 9/2018 | |
| WO | WO 2018/173053 | 9/2018 | |

OTHER PUBLICATIONS

Advisory Action dated Jun. 16, 2020 from the US Patent and Trademark Office Re. U.S. Appl. No. 13/449,539. (5 pages).
Applicant-Initiated Interview Summary dated Apr. 2, 2019 From the US Patent and Trademark Office Re. U.S. Appl. No. 13/905,224. (3 pages).
Applicant-Initiated Interview Summary dated Jan. 4, 2016 From the US Patent and Trademark Office Re. U.S. Appl. No. 13/449,539.
Applicant-Initiated Interview Summary dated Jul. 14, 2016 From the US Patent and Trademark Office Re. U.S. Appl. No. 13/449,539.
Applicant-Initiated Interview Summary dated Nov. 14, 2018 From the US Patent and Trademark Office Re. U.S. Appl. No. 13/449,539. (3 pages).
Applicant-Initiated Interview Summary dated Jan. 21, 2015 From the US Patent and Trademark Office Re. U.S. Appl. No. 13/449,539.
Applicant-Initiated Interview Summary dated Feb. 22, 2016 From the US Patent and Trademark Office Re. U.S. Appl. No. 13/880,066.
Applicant-Initiated Interview Summary dated Jan. 24, 2014 From the US Patent and Trademark Office Re. U.S. Appl. No. 13/449,539.
Applicant-Initiated Interview Summary dated Apr. 25, 2018 From the US Patent and Trademark Office Re. U.S. Appl. No. 14/394,276. (3 pages).
Applicant-Initiated Interview Summary dated Sep. 28, 2016 From the US Patent and Trademark Office Re. U.S. Appl. No. 13/905,224.

Communication Pursuant to Article 94(3) EPC dated Dec. 2, 2020 From the European Patent Office Re. Application No. 15862313.2. (9 Pages).
Communication Pursuant to Article 94(3) EPC dated Nov. 4, 2014 From the European Patent Office Re. Application No. 11833950.6.
Communication Pursuant to Article 94(3) EPC dated Feb. 8, 2016 From the European Patent Office Re. Application No. 11833950.6.
Communication Pursuant to Article 94(3) EPC dated Apr. 10, 2015 From the European Patent Office Re. Application No. 11782222.1.
Communication Pursuant to Article 94(3) EPC dated Jun. 10, 2014 From the European Patent Office Re. Application No. 117822476.3.
Communication Pursuant to Article 94(3) EPC dated Jun. 10, 2014 From the European Patent Office Re. Application No. 11784782.2.
Communication Pursuant to Article 94(3) EPC dated Apr. 14, 2014 From the European Patent Office Re. Application No. 11782221.3.
Communication Pursuant to Article 94(3) EPC dated Jul. 20, 2016 From the European Patent Office Re. Application No. 11782221.3.
Communication Pursuant to Article 94(3) EPC dated Sep. 26, 2014 From the European Patent Office Re. Application No. 11782222.1.
Communication Pursuant to Article 94(3) EPC dated Jul. 27, 2016 From the European Patent Office Re. Application No. 11782222.1.
Communication Pursuant to Article 94(3) EPC dated Oct. 30, 2014 From the European Patent Office Re. Application No. 11782221.3.
Communication Pursuant to Rule 164(1) EPC: Supplementary Partial European Search Report and the European Provisional Opinion dated May 18, 2018 From the European Patent Office Re. Application No. 15862313.2. (15 Pages).
Decision of Rejection dated Apr. 28, 2016 From the Japanese Patent Office Re. Application No. 2013-534435 and Its Machine Translation in English.
Final Official Action dated Jun. 3, 2021 From the US Patent and Trademark Office Re. U.S. Appl. No. 13/905,224. (17 Pages).
International Preliminary Report on Patentability dated May 2, 2013 From the International Bureau of WIPO Re. Application No. PCT/IB2011/054634.
International Preliminary Report on Patentability dated May 2, 2013 From the International Bureau of WIPO Re. Application No. PCT/IB2011/054635.
International Preliminary Report on Patentability dated May 2, 2013 From the International Bureau of WIPO Re. Application No. PCT/IB2011/054636.
International Preliminary Report on Patentability dated May 2, 2013 From the International Bureau of WIPO Re. Application No. PCT/IB2011/054638.
International Preliminary Report on Patentability dated May 2, 2013 From the International Bureau of WIPO Re. Application No. PCT/IB2011/054639.
International Preliminary Report on Patentability dated May 2, 2013 From the International Bureau of WIPO Re. Application No. PCT/IB2011/054640.
International Preliminary Report on Patentability dated May 2, 2013 From the International Bureau of WIPO Re. Application No. PCT/IB2011/054641.
International Preliminary Report on Patentability dated Dec. 3, 2015 From the International Bureau of WIPO Re. Application No. PCT/IL2014/050457.
International Preliminary Report on Patentability dated Oct. 3, 2019 From the International Bureau of WIPO Re. Application No. PCT/IL2018/050321. (11 Pages).
International Preliminary Report on Patentability dated Oct. 3, 2019 From the International Bureau of WIPO Re. Application No. PCT/IL2018/050322. (16 Pages).
International Preliminary Report on Patentability dated Aug. 7, 2014 From the International Bureau of WIPO Re. Application No. PCT/IL2013/050068.
International Preliminary Report on Patentability dated Jun. 8, 2017 From the International Bureau of WIPO Re. Application No. PCT/IL2015/051145. (16 Pages).
International Preliminary Report on Patentability dated Oct. 30, 2014 From the International Bureau of WIPO Re. Application No. PCT/IL2013/050339.

(56) References Cited

OTHER PUBLICATIONS

International Preliminary Report on Patentability dated Oct. 30, 2014 From the International Bureau of WIPO Re. Application No. PCT/IL2013/050341.
International Search Report and the Written Opinion dated May 2, 2016 From the International Searching Authority Re. Application No. PCT/IL2015/051145.
International Search Report and the Written Opinion dated Feb. 7, 2012 From the International Searching Authority Re. Application No. PCT/IB2011/054641.
International Search Report and the Written Opinion dated Oct. 11, 2013 From the International Searching Authority Re. Application No. PCT/IL2013/050341.
International Search Report and the Written Opinion dated Sep. 19, 2013 From the International Searching Authority Re. Application No. PCT/IL2013/050068.
International Search Report and the Written Opinion dated Nov. 20, 2014 From the International Searching Authority Re. Application No. PCT/IL2014/050457.
International Search Report and the Written Opinion dated Jun. 22, 2012 From the international Searching Authority Re. Application No. PCT/IB2011/054640.
International Search Report and the Written Opinion dated Jan. 23, 2012 From the International Searching Authority Re. Application No. PCT/IB2011/054635.
International Search Report and the Written Opinion dated Jan. 25, 2012 From the International Searching Authority Re. Application No. PCT/IB2011/054636.
International Search Report and the Written Opinion dated Jan. 27, 2012 From the International Searching Authority Re. Application No. PCT/IB2011/054634.
International Search Report and the Written Opinion dated Jan. 27, 2012 From the International Searching Authority Re. Application No. PCT/IB2011/054638.
International Search Report and the Written Opinion dated Aug. 28, 2018 From the International Searching Authority Re. Application No. PCT/IL2018/050322. (40 Pages).
International Search Report and the Written Opinion dated Aug. 29, 2018 From the International Searching Authority Re. Application No. PCT/IL2018/050321. (16 Pages).
International Search Report and the Written Opinion dated Oct. 29, 2013 From the International Searching Authority Re. Application No. PCT/IL2013/050339.
International Search Report and the Written Opinion dated Jan. 31, 2012 From the International Searching Authority Re. Application No. PCT/IB2011/054639.
Invitation Pursuant to Rule 137(4) EPC dated Apr. 4, 2014 From the European Patent Office Re. Application No. 11785792.0.
Invitation Pursuant to Rule 137(4) EPC dated Apr. 8, 2014 From the European Patent Office Re. Application No. 11782222.1.
Invitation Pursuant to Rule 137(4) EPC dated Apr. 10, 2014 From the European Patent Office Re. Application No. 11782476.3.
Invitation Pursuant to Rule 137(4) EPC dated Mar. 21, 2016 From the European Patent Office Re. Application No. 11782222.1.
Invitation to Pay Additional Fees dated Sep. 3, 2013 From the International Searching Authority Re. Application No. PCT/IL2013/050339.
Invitation To Pay Additional Fees dated Mar. 4, 2016 From the International Searching Authority Re. Application No. PCT/IL2015/051145.
Invitation to Pay Additional Fees dated Sep. 4, 2014 From the International Searching Authority Re. Application No. PCT/IL2014/050457.
Invitation to Pay Additional Fees dated Aug. 5, 2013 From the International Searching Authority Re. Application No. PCT/IL2013/050341.
Invitation to Pay Additional Fees dated Apr. 17, 2012 From the International Searching Authority Re. Application No. PCT/IB2011/054640.
Invitation to Pay Additional Fees dated Jun. 21, 2018 From the International Searching Authority Re. Application No. PCT/IL2018/050322. (3 Pages).
Invitation to Pay Additional Fees dated Jul. 24, 2013 From the International Searching Authority Re. Application No. PCT/IL2013/050068.
Invitation to Pay Additional Fees dated Jun. 25, 2018 From the International Searching Authority Re. Application No. PCT/IL2018/050321. (2 Pages).
Notice of Allowance dated Mar. 6, 2019 From the US Patent and Trademark Office Re. U.S. Appl. No. 14/394,276. (11 Pages).
Notice of Allowance dated Oct. 6, 2014 From the US Patent and Trademark Office Re. U.S. Appl. No. 13/880,061.
Notice of Allowance dated Nov. 7, 2013 From the US Patent and Trademark Office Re. U.S. Appl. No. 13/049,013.
Notice of Allowance dated Dec. 8, 2015 From the US Patent and Trademark Office Re. U.S. Appl. No. 14/049,238.
Notice of Allowance dated Jan. 8, 2015 From the US Patent and Trademark Office Re. U.S. Appl. No. 13/880,061.
Notice of Allowance dated Aug. 11, 2020 from the US Patent and Trademark Office Re. U.S. Appl. No. 13/449,539. (11 pages).
Notice of Allowance dated Sep. 14, 2016 From the US Patent and Trademark Office Re. U.S. Appl. No. 13/879,400.
Notice of Allowance dated Jul. 18, 2016 From the US Patent and Trademark Office Re. U.S. Appl. No. 13/879,400.
Notice of Allowance dated Jun. 21, 2013 From the US Patent and Trademark Office Re. U.S. Appl. No. 13/049,151.
Notice of Allowance dated Sep. 23, 2020 from the US Patent and Trademark Office Re. U.S. Appl. No. 14/889,890. (8 pages).
Notice of Allowance dated Mar. 26, 2019 From the US Patent and Trademark Office Re. U.S. Appl. No. 14/190,113. (8 pages).
Notice of Non-Compliant Amendment dated Sep. 23, 2015 From the US Patent and Trademark Office Re. U.S. Appl. No. 13/880,124.
Notice of Reason for Rejection dated Aug. 25, 2015 From the Japanese Patent Office Re. Application No. 2013-534435.
Notification of Office Action and Search Report dated Apr. 1, 2021 From the State Intellectual Property Office of the People's Republic of China Re. Application No. 201880031396.2 and Its Translation of Office Action Into English. (9 Pages).
Notification of Office Action and Search Report dated Dec. 1, 2014 From The State Intellectual Property Office of the People's Republic of China Re. Application No. 201180060862.8.
Office Action dated Jul. 30, 2014 From The State Intellectual Property Office of the People's Republic of China Re. Application No. 201180060741.3 and Its Summary in English.
Official Action dated Jul. 2, 2015 From the US Patent and Trademark Office Re. U.S. Appl. No. 13/879,400.
Official Action dated Dec. 3, 2014 From the US Patent and Trademark Office Re. U.S. Appl. No. 13/462,956.
Official Action dated Jun. 3, 2016 From the US Patent and Trademark Office Re. U.S. Appl. No. 13/880,066.
Official Action dated Jun. 3, 2019 From the US Patent and Trademark Office Re. U.S. Appl. No. 13/449,539. (13 Pages).
Official Action dated Nov. 3, 2017 From the US Patent and Trademark Office Re. U.S. Appl. No. 14/394,276. (11 pages).
Official Action dated Nov. 4, 2014 From the US Patent and Trademark Office Re. U.S. Appl. No. 13/879,400.
Official Action dated Aug. 5, 2015 From the US Patent and Trademark Office Re. U.S. Appl. No. 13/905,224.
Official Action dated Jan. 5, 2016 From the US Patent and Trademark Office Re. U.S. Appl. No. 13/880,124.
Official Action dated Jun. 5, 2015 From the US Patent and Trademark Office Re. U.S. Appl. No. 14/049,238.
Official Action dated Nov. 5, 2014 From the US Patent and Trademark Office Re. U.S. Appl. No. 13/049,022.
Official Action dated Feb. 6, 2015 From the US Patent and Trademark Office Re. U.S. Appl. No. 14/190,113.
Official Action dated Jan. 6, 2017 From the US Patent and Trademark Office Re. U.S. Appl. No. 14/190,113. (11 pages).
Official Action dated Oct. 7, 2014 From the US Patent and Trademark Office Re. U.S. Appl. No. 13/880,109.
Official Action dated May 8, 2013 From the US Patent and Trademark Office Re. U.S. Appl. No. 13/462,956.

(56) References Cited

OTHER PUBLICATIONS

Official Action dated Aug. 10, 2018 From the US Patent and Trademark Office Re. U.S. Appl. No. 14/190,113. (11 pages).
Official Action dated Jun. 10, 2016 From the US Patent and Trademark Office Re. U.S. Appl. No. 14/190,113.
Official Action dated Mar. 10, 2016 From the US Patent and Trademark Office Re. U.S. Appl. No. 13/449,539.
Official Action dated Sep. 10, 2014 From the US Patent and Trademark Office Re. U.S. Appl. No. 14/049,238.
Official Action dated Oct. 11, 2018 From the US Patent and Trademark Office Re. U.S. Appl. No. 14/394,276. (200 Pages).
Official Action dated Sep. 11, 2015 From the US Patent and Trademark Office Re. U.S. Appl. No. 13/880,066.
Official Action dated Apr. 13, 2020 from the US Patent and Trademark Office Re. U.S. Appl. No. 14/889,890. (23 pages).
Official Action dated Aug. 13, 2020 from the US Patent and Trademark Office Re. U.S. Appl. No. 13/905,224. (24 pages).
Official Action dated Apr. 14, 2014 From the US Patent and Trademark Office Re. U.S. Appl. No. 13/879,400.
Official Action dated Aug. 14, 2015 From the US Patent and Trademark Office Re. U.S. Appl. No. 13/449,539.
Official Action dated May 16, 2019 From the US Patent and Trademark Office Re. U.S. Appl. No. 15/529,137. (11 pages).
Official Action dated Oct. 16, 2019 From the US Patent and Trademark Office Re. U.S. Appl. No. 13/449,539.(8 Pages).
Official Action dated Jul. 17, 2013 From the US Patent and Trademark Office Re. U.S. Appl. No. 13/049,013.
Official Action dated Nov. 17, 2017 From the US Patent and Trademark Office Re. U.S. Appl. No. 13/905,224. (19 pages).
Official Action dated Dec. 19, 2013 From the US Patent and Trademark Office Re. U.S. Appl. No. 13/049,022.
Official Action dated Mar. 20, 2014 From the US Patent and Trademark Office Re. U.S. Appl. No. 13/449,539.
Official Action dated Oct. 20, 2017 From the US Patent and Trademark Office Re. U.S. Appl. No. 14/190,113. (7 pages).
Official Action dated Apr. 21, 2017 From the US Patent and Trademark Office Re. U.S. Appl. No. 14/394,276. (13 pages).
Official Action dated Feb. 21, 2019 From the US Patent and Trademark Office Re. U.S. Appl. No. 14/889,890. (19 pages).
Official Action dated Jun. 21, 2018 From the US Patent and Trademark Office Re. U.S. Appl. No. 13/449,539. (8 pages).
Official Action dated Apr. 23, 2014 From the US Patent and Trademark Office Re. U.S. Appl. No. 13/880,061.
Official Action dated Oct. 24, 2012 From the US Patent and Trademark Office Re. U.S. Appl. No. 13/049,013.
Official Action dated Oct. 24, 2019 From the US Patent and Trademark Office Re. U.S. Appl. No. 14/889,890. (54 pages).
Official Action dated Sep. 25, 2013 From the US Patent and Trademark Office Re. U.S. Appl. No. 13/462,956.
Official Action dated Sep. 25, 2015 From the US Patent and Trademark Office Re. U.S. Appl. No. 14/190,113.
Official Action dated Jul. 26, 2016 From the US Patent and Trademark Office Re. U.S. Appl. No. 13/880,124.
Official Action dated Dec. 27, 2016 From the US Patent and Trademark Office Re. U.S. Appl. No. 13/449,539. (13 pages).
Official Action dated Apr. 29, 2016 From the US Patent and Trademark Office Re. U.S. Appl. No. 13/905,224.
Official Action dated Aug. 29, 2013 From the US Patent and Trademark Office Re. U.S. Appl. No. 13/449,539.
Official Action dated Jan. 29, 2013 From the US Patent and Trademark Office Re. U.S. Appl. No. 13/049,151.
Official Action dated Oct. 31, 2018 From the US Patent and Trademark Office Re. U.S. Appl. No. 13/905,224. (23 pages).
Restriction Official Action dated Jan. 4, 2019 From the US Patent and Trademark Office Re. U.S. Appl. No. 15/529,137. (8 pages).
Restriction Official Action dated Oct. 5, 2012 From the US Patent and Trademark Office Re. U.S. Appl. No. 13/049,151.
Restriction Official Action dated Jul. 7, 2014 From the US Patent and Trademark Office Re. U.S. Appl. No. 14/049,238.
Restriction Official Action dated Apr. 14, 2015 From the US Patent and Trademark Office Re. U.S. Appl. No. 13/880,124.
Restriction Official Action dated Nov. 17, 2014 From the US Patent and Trademark Office Re. U.S. Appl. No. 13/880,066.
Restriction Official Action dated May 24, 2018 From the US Patent and Trademark Office Re. U.S. Appl. No. 14/889,890. (8 pages).
Restriction Official Action dated Feb. 27, 2015 From the US Patent and Trademark Office Re. U.S. Appl. No. 13/905,224.
Restriction Official Action dated Mar. 27, 2015 From the US Patent and Trademark Office Re. U.S. Appl. No. 13/880,095.
Restriction Official Action dated Oct. 27, 2016 From the US Patent and Trademark Office Re. U.S. Appl. No. 14/394,276.
Restriction Official Action dated Jun. 28, 2013 From the US Patent and Trademark Office Re. U.S. Appl. No. 13/449,539.
Restriction Official Action dated Aug. 30, 2012 From the US Patent and Trademark Office Re. U.S. Appl. No. 13/049,013.
Restriction Official Action dated Oct. 30, 2014 From the US Patent and Trademark Office Re. U.S. Appl. No. 13/880,083.
Search Report dated Jul. 17, 2014 From The State Intellectual Property Office of the People's Republic of China Re. Application No. 201180060741.3 and Its Machine Translation in English.
Supplementary European Search Report and the European Search Opinion dated Dec. 4, 2020 From the European Patent Office Re. Application No. 18771348.2. (9 Pages).
Supplementary European Search Report and the European Search Opinion dated Sep. 5, 2018 From the European Patent Office Re. Application No. 15862313.2. (13 Pages).
Supplementary European Search Report and the European Search Opinion dated Dec. 22, 2016 From the European Patent Office Re. Application No. 14801877.3. (9 Pages).
Supplementary European Search Report dated Mar. 12, 2014 From the European Patent Office Re. Application No. 11833950.6.
Translation Dated Mar. 12, 2015 of Notification of Office Action and Search Report dated Dec. 1, 2014 From The State Intellectual Property Office of the People's Republic of China Re. Application No. 201180060862.8.
Translation Dated Nov. 18, 2015 of Notice of Reason for Rejection dated Aug. 25, 2015 From the Japanese Patent Office Re. Application No. 2013-534435.
Ahmed et al. "Renal Sympathetic Denervation Using An Irrigated Radiofrequency Ablation Catheter for the Management of Drug-Resistant Hypertension", Journal of the American College of Cardiology: Cardiovascular Interventions, JACC, 5(7): 758-765, 2012.
Ali et al. "Signal Processing Overview of Ultrasound Systems for Medical Imaging", Texas Instruments White Paper, SPRAB12: 1-27, Nov. 2008.
Anonymus "Indication for and Results of Sympathectomy in Patients With Peripheral Vascular Disease", Lumbar Sympathectomy, Poster, 34 P., 2009.
Aovama et al. "Comparison of Cryothermia and Radiofrequency Current in Safety and Efficacy of Catheter Ablation Within the Canine Coronary Sinus Close to the Left Circumflex Coronary Artery", Journal of Cardiovascular Electrophysiology, 16: 1218-1226, Nov. 2005.
Atherton et al. "Micro-Anatomy of the Renal Sympathetic Nervous System: A Human Postmortem Histologic Study", Clinical Anatomy, p. 1-6, Oct. 4, 2011.
Bailey et al. "Cavitation Detection During Shock-Wave Lithotripsy", Ultrasound in Medicine and Biology, XP027605630, 31(9): 1245-1256, Sep. 1, 2005. Abstract, Fig.1, p. 1246, p. 1247, r-h col. p. 1249, r-h Col.
Baker et al. "Operative Lumbar Sympathectomy for Severe Lower Limb Ischaemia: Still A Valuable Treatment Option", Annals of the Royal College of Surgeons of England, 76(1): 50-53, Jan. 1994.
Bambi et al. "Real-Time Digital Processing of Doppler Ultrasound Signals", IEEE International Conference on Acoustics, Speech, and Signal Processing, Proceedings, (ICASSP '05), (5): v/977-v/980, Mar. 23-23, 2005.
Bandyopadhyay et al. "Outcomes of Beta-Blocker Use in Pulmonary Arterial Hypertension: A Propensity-Matched Analysis", European Respiratory Journal, 46(3): 750-760, Published Online May 28, 2015.

(56) References Cited

OTHER PUBLICATIONS

Bharat et al. "Monitoring Stiffness Changes in Lesions After Radiofrequency Ablation at Different Temperatures and Durations of Ablation", Ultrasound in Medicine & Biology, 31(3): 415-422, 2005.
Bhatt et al. "A Controlled Trial of Renal Denervation for Resistant Hypertension", The New England Journal of Medicine, 270(15): 1393-1401, Published Online Mar. 29, 2014.
Blankestijn et al. "Renal Denervation: Potential Impact on Hypertension in Kidney Disease?", Nephrology, Dialysis, Transplantation, 26(9): 2732-2734, Apr. 19, 2011.
Brandt et al. "Effects of Renal Sympathetic Denervation on Arterial Stiffness and Central Hemodynamics in Patients With Resistant Hypertension", Journal of the American College of Cardiology, 60(19): 1956-1965, 2012.
Brandt et al. "Renal Sympathetic Denervation Reduces Left Ventricular Hypertrophy and Improves Cardiac Function in Patients With Resistant Hypertension", Journal of the American College of Cardiology, 59(10): 901-909, 2012.
Brasselet et al. "Effect of Local Heating on Restenosis and In-Stent Neointimal Hyperplasia in the Atherosclerotic Rabbit Model: A Dose-Ranging Study", European Heart Journal, 29: 402-412, 2008.
Brinton et al. "Externally Focused Ultrasound for Sympathetic Renal Denervation", WAVE I First-In-Man Study, Kona Medical Inc., PowerPoint Presentation, TCT 2012, 15 P., 2012.
Campese et al. "Renal Afferent Denervation Prevents the Progression of Renal Disease in the Renal Ablation Model of Chronic Renal Failure in the Rat", American Journal of Kidney Diseases, 26(5): 861-865, Nov. 1995. Abstract.
Campese et al. "Sympathetic Renal Innervation and Resistant Hypertension", International Journal of Hypertension, 2011(Art.ID 814354): 1-6, 2011.
Cardiosonic "Cardiosonic New Applications", Cardiosonic, p. 1-20, Mar. 2014.
Cardiosonic "Histological Map of Swine Pulmonary Arteries", Cardiosonic, Animal #223, Mar. 26, 2014.
Cardiosonic "Histological Map of Swine Pulmonary Arteries", Cardiosonic, Animal #234, Mar. 18, 2014.
Cardiosonic "Histological Map of Swine Pulmonary Arteries", Cardiosonic, Animal #234, Mar. 26, 2014.
Cardiosonic "Histopathology Report", Cardiosonic, 2 P., Dec. 26, 2013.
Cardiosonic "PA/Trachea—Feedback Provisional", Cardiosonic, 5 P, Jun. 9, 2014.
Cardiosonic "PAH Preliminary Development Meeting Minutes", Cardiosonic. 2 P., Mar. 23, 2014.
Chen et al. "Artery Denervation to Treat Pulmonary Arterial Hypertension. The Single-Center, Prospective, First-in-Man PADN-1 Study (First-in-Man Pulmonary Artery Denervation for Treatment of Pulmonary Artery Hypertension)", Journal of the American College of Cardiology, JACC, 62(12): 1092-1100, Sep. 17, 2013.
Chen et al. "Hemodynamic, Functional, and Clinical Responses to Pulmonary Artery Denervation in Patients With Pulmonary Arterial Hypertension of Different Causes: Phase II Results From the Pulmonary Artery Denervation-1 Study", Circulation: Cardiovascular Interventions, 8(11): e002837-1-e002837-10, Nov. 9, 2015.
Chen et al. "Percutaneous Pulmonary Artery Denervation Completely Abolishes Experimental Pulmonary Arterial Hypertension In Vivo", EuroIntervention, 9(2): 269-276, Jun. 22, 2013.
Ciarka et al. "Prognostic Significance of Sympathetic Nervous System Activation in Pulmonary Arterial Hypertension", American Journal of Respiratory and Critical Care Medicine, 181(11): 1269-1275, Published Online Mar. 1, 2010.
CIBIS-II Investigators and Committees "The Cardiac Insufficiency Bisoprolol Study II (CIBIS-II): A Randomised Trial", The Lancet, 353(9146): 9-13, Jan. 2, 1999.
Cohn et al. "A Comparison of Enalapril With Hydralazine-Isosorbide Dinitrate in the Treatment of Chronic Congestive Heart Failure", The New England Journal of Medicine, 325(5): 303-310, Aug. 1, 1991.

Consensus Trial Study Group "Effects of Enalapril on Mortality in severe Congestive Heart Failure. Results of the Cooperative North Scandinavian Enalapril Survival Study (CONSENSUS)", The New England Journal of Medicine, 316(23): 1429-1435, Jun. 4, 1987.
Copty et al. "Localized Heating of Biological Media Using A 1-W Microwave Near-Field Probe", IEEE Transactions on Microwave Theory and Techniques, 52(8): 1957-1963, Aug. 2004.
Copty et al. "Low-Power Near-Field Microwave Applicator for Localized Heating of Soft Matter", Applied Physics Letters, 84(25): 5109-5111, Jun. 21, 2004.
Damianou et al. "Dependence of Ultrasonic Attenuation and Absorpteion in Dog Soft Tissues on Temperature and Thermal Dose", Journal of the Acoustical Society of America, 102(1): 628-634, Jul. 1997.
Davies et al. "First-in-Man Safety Evaluation of Renal Denervation for Chronic Systolic Heart Failure: Primary Outcome From REACH-Pilot Study", International Journal of Cardiology, 162: 189-192, 2013.
De Man et al. "Bisoprolol Delays Progression Towards Right Heart Failure in Experimental Pulmonary Hypertension", Circulation Heart Failure, 5(1): 97-105, Published Online Dec. 9, 2011.
De Man et al. "Neurohormonal Axis in Patients With Pulmonary Arterial Hypertension. Friend or Foe?", American Journal of Respiratory and Critical Care Medicine, 187(1): 14-19, Published Online Nov. 9, 2012.
Deneke et al. "Histopathology of Intraoperatively Induced Linear Radiofrequency Ablation Lesions in Patients With Chronic Atrial Fibrillation", European Heart Journal, 26: 1797-1803, 2005.
Dewhirst et al. "Basic Principles of Thermal Dosimetry and Thermal Thresholds for Tissue Damage From Hyperthermia", International Journal of Hyperthermia, 19(3): 267-294, May-Jun. 2003.
DiBona "Neural Control of Renal Function: Cardiovascular Implications", Hypertension, 13: 539-548, 1989.
DiBona "Neural Control of the Kidney: Past, Present, and Future", Hypertension, 41: 621-624, Dec. 16, 2002.
DiBona "Physiology in Perspective: The Wisdom of the Body. Neural Control of the Kidney", American Journal of Physiology, Regulatory, Integrative and Comparative Physiology, 289(3): R633-R641, Sep. 2005.
DiBona et al. "Differentiated Sympathetic Neural Control of the Kidney", American Journal of Physiology, 271: R84-R90, 1996.
DiBona et al. "Translational Medicine: The Antihypertensive Effect of Renal Denervation", American Journal of Physiology, Regulatory, Integrative and Comparative Physiology, 298(2): R245-R253, Feb. 2010.
Diederich et al. "Catheter-Based Ultrasound Applicators for Selective Thermal Ablation: Progress Towards MRI-Guided Applications in Prostate", International Journal of Hyperthermia, 20(7): 739-756, Nov. 2004.
Diederich et al. "Catheter-Based Ultrasound Devices and MR Thermal Monitoring for Conformal Prostate Thermal Therapy", 30th Annual International IEEE EMBS Conference, Vancouver, British Columbia, Canada, Aug. 20-24, 2008, p. 3664-3668, 2008.
Diederich et al. "Induction of Hyperthermia Using An Intracavitary Multielement Ultrasonic Applicator", IEEE Transactions on Biomedical Engineering, 36(4): 432-438, Apr. 1989.
Diederich et al. "Ultrasound Technology for Hyperthermia", Ultrasound in Medicine & Biology, 25(6): 871-887, 1999.
Donoho et al. "Stable Recovery of Sparse Overcomplete Representations in the Presence of Noise", IEEE Transactions on Information Theory, 52(1): 1-42, Jan. 2006.
Drake et al. "Problematic Anatomical Sites Around the Pulmonary Artery", Gray's Anatomy for Students, 9 P., 2004.
Esler "The 2009 Carl Ludwig Lecture: Pathophysiology of the Human Sympathetic Nervous System in Cardiovascular Diseases: The Transition From Mechanisms to Medical Management", Journal of Applied Physiology, 108: 227-237, 2010.
Esler et al. "Measurement of Total and Organ-Specific Norepinephrine Kinetics in Humans", American Journal of Physiology—Endocrinology Metabolism 10, 247(1/Pt. 1): E21-E28, Jul. 1984.
Esler et al. "Renal Sympathetic Denervation for Treatment of Drug-Resistant Hypertension: One-Year Results From the Symplicity HTN-2 Randomized, Controlled Trial", Circulation, 126: 2976-2982, 2012.

(56) References Cited

OTHER PUBLICATIONS

Failla et al. "Sympathetic Tone Restrains Arterial Distensibility of Healthy and Atherosclerotic Subjects", Journal of Hypertension, 17: 1117-1123, 1999.
Fischell PeriVascular Renal Denervation (PVRD™), Ablative Solutions Inc., TransCatheter Therapeutics Meeting, Miami, FL, USA, Oct. 24, 2012, PowerPoint Presentation, 14 P., Oct. 2012.
Fort Wayne Metals "HHS Tube", Fort Wayne Metals Research Products Corporation, 2 P., 2009.
Fujikura et al. "Effects of Ultrasonic Exposure Parameters on Myocardial Lesions Induced by High-Intensity Focused Ultrasound", Journal of Ultrasound Medicine, 25: 1375-1386, 2006.
Galie et al. "2015 ESC/ERS Guidelines for the Diagnosis and Treatment of Pulonary Hypertension. The Joint Task Force for the Diagnosis and Treatment of Pulmonary Hypertension of the European Society of Cardiology (ESC) and the European Respiratory Society (ERS). Endorsed by: Association for European Paediatric and Congenital Cardiology (AEPC), International Society for Heart and Lung Transplantation (ISHLT)", European Heart Journal, 37(1): 67-119, Published Online Aug. 29, 2015.
Galie et al. "New Treatment Stategies for Pulmonary Arterial Hypertension. Hopes or Hypes?", Journal of the American College of Cardiology, 62(12): 1101-1102, Sep. 17, 2013.
Galie et al. "Updated Treatment Algorithm of Pulmonary Arterial Hypertension", Journal of the American College of Cardiology, 62(25/Suppl.D): D60-D72, 2013.
Gander et al. "Least-Squares Fitting of Circles and Ellipses", BIT Numerical Mathematics, 34(4): 558-578, Dec. 1994.
Giering et al. "Determination of the Specific Heat Capacity of Healthy and Tumorous Human Tissue", Thermochimica Acta, 251: 199-205, Mar. 1995.
Glazier et al. "Laser Balloon Angioplasty Combined With Local Intrcoronary Heparin Therapy: Immediate and Short-Term Follow-Up Results", American Heart Journal, 134: 266-273, 1997.
Goswami "Renal Denervation: A Percutaneous Therapv for HTN", Prairie Heart Institute, Synvacor, The VEINS: Venous Endovascular Interventions Strategies. Chicago, USA, 42 P., 2012.
Granada et al. "A Translational Overview for the Evaluation of Peri-Renal Denervation Technologies", Cardiovascular Research Foundation, Columbai University Medical Center. New York, USA, Alizee Pathology, 25 P., 2011.
Grassi et al. "Sympathetic Mechanisms, Organ Damage, and Antihypertensive Treatment", Current Hypertension Report, 13: 303-308, 2011.
Griffiths et al. "Thoraco-Lumbar Splanchnicectomy and Sympathectomy. Anaesthetic Procedure", Anaesthesia, 3(4): 134-146, Oct. 1948.
Grimson et al. "Total Thoracic and Partial to Total Lumbar Sympathectomy, Splanchnicectomy and Celiac Ganglionectomy for Hypertension", Annals of Surgery, 138(4): 532-547, Oct. 1953.
Heath et al. "The Structure of the Pulmonary Trunk at Different Ages and in Cases of Pulmonary Hypertension and Pulmonary Stenosis", The Journal of Pathology and Bacteriology, 77(2): 443-456, Apr. 1959.
Hering et al. "Renal Denervation in Moderate to Severe CKD", Journal of the American Society of Nephrology, 23: 1250-1257, 2012.
Hering et al. "Substantial Reduction in Single Sympathetic Nerve Firing After Renal Denervation in Patients With rRsistant Hypertension", Hypertension, 61:1-14, Nov. 19, 2012.
Holdaas et al. "Modulation of Reflex Renal Vasoconstriction by Increased Endogenous Renal Prostaglandin Synthesis", The Journal of Pharmacology and Experimental Therapeutics, 232(3): 725-731, 1985.
Humbert et al. "Advances in Therapeutic Interventions for Patients With Pulmonary Arterial Hypertension", Circulation, XP055531396, 130(24): 2189-2208, Published Online Dec. 9, 2014.
Janssen et al. "Role of Afferent Renal Nerves in Spontaneous Hypertension in Rats", Hypertension, 13: 327-333, 1989.

Joner "Histopathological Characterization of Renal Arteries After Radiofrequency Catheter Based Sympathetic Denervation in A Healthy Porcine Model", Deutsches Herzzentrum M?nchen, Technische Universit?t M?nchen, PowerPoint Presentation, TCT 2012, 15 P., 2012.
Katholi "Renal Nerves in the Pathogenesis of Hypertension in Experimental Animals and Humans". American Journal of Physiology, 245: F1-F14, 1983.
Katholi et al. "Intrarenal Adenosine Produces Hypertension by Activating the Sympathetic Nervous System Via the Renal Nerves in the Dog", Journal of Hypertension, 2: 349-359, 1984.
Katholi et al. "Renal Nerves in the Maintenance of Hypertension: A Potential Therapeutic Target", Current Hypertension Reports, 12(3): 196-204, Jun. 2010.
Kleinlogel et al. "A Gene-Fusion Strategy for Stoichiometric and Co-Localized Expression of Light-Gated Membrane Proteins", Nature Methods, 8(12): 1083-1091, Dec. 2011.
Kline et al. "Functional Reinnervation and Development of Supersensitivity to NE After Renal Denervation in Rats", American Journal of Physiology, 238: R353-R358, 1980.
Kolh "Carotid Denervation by Adventitial Stripping: A Promising Treatment of Carotid Sinus Syndrome?", European Journal of Vascular and Endovascular Surgery, 39(2): 153-154, Feb. 2010.
Krum et al. "Catheter-Based Renal Sympathetic Denervation for Resistant Hypertension: A Multicentre Safety and Proof-of-Principle Cohort Study", The Lancet, 373: 1275-1281, Apr. 11, 2009.
Krum et al. "Catheter-Based Renal Sympathetic Denervation for Resistant Hypertension: A Multicentre Safety and Proof-of-Principle Cohort Study", The Lancet, 373: 1275-1281, Mar. 30, 2009.
Kummer "Pulmonary Vascular Innervation and Its Role in Responses to Hypoxia: Size Matters!", Proceedings of the American Thoracic Society, 8(6): 471-476, Nov. 1, 2011.
Lafon "Miniature Devices for Minimallv Invasive Thermal Ablation by High Intensity Ultrasound", Cargese Workshop 2009, University of Lyon, France, INSERM U556, Presentation, 39 P., 2009.
Lambert et al. "Redo of Percutaneous Renal Denervation in A Patient With Recurrent Resistant Hypertension After Primary Treatment Success", Catheterization and Cardiovascular Interventions, p. 1-11, 2012.
Lele "Effects of Focused Ultrasonic Radiation on Peripheral Nerve, With Observations on Local Heating", Experimental Neurology, 8: 47-83, 1963.
Lemoine et al. "Amputations and Sympathectomy in Peripheral Vascular Disease of the Lower Extremity. Experience With 180 Patients", Journal of the National Medical Association, 61(3): 219-221, May 1969.
Li et al. "Acoustic Proximity Ranging in the Presence of Secondary Echoes", IEEE Transactions on Instrumentation and Measurement, XP011102759, 52(5): 1593-1605, Oct. 1, 2003. p. 1593.
Lin et al. "Utility of the PlasmaKinetic™ Bipolar Forceps® for Control of the Renal Artery in A Porcine Model", JTUA, 14(3): 118-121, Sep. 2003.
Liu et al. "A Helical Microwave Antenna for Welding Plaque During Balloon Angioplasty", IEEE Transactions on Microwave Theory and Techniques, 44(10): 1819-1831, Oct. 1996.
Liu et al. "Pulmonary Artery Denervation Improves Pulmonary Arterial Hypertension Induced Right Ventricular Dysfunction by Modulating the Local Renin-Angiotensin-Aldosterone System", BMC Cardiovascular Disorders, 16(1): 192-1-192-10, Oct. 10, 2016.
Lopez et al. "Effects of Sympathetic Nerves on Collateral Vessels in the Limb of Atherosclerosis Primates", Atherosclerosis, 90: 183-188, 1991.
Mabin et al. "First Experience With Endovascular Ultrasound Renal Denervation for the Treatment of Resistant Hypertension", EuroIntervention, 8: 57-61, 2012.
Mahfoud et al. "Effect of Renal Sympathetic Denervation on Glucose Metabolism in Patients With Resistant Hypertension: A Pilot Study", Circulation, 123: 1940-1946, 2011.

(56) References Cited

OTHER PUBLICATIONS

Mahfoud et al. "Is There A Role for Renal Sympathetic Denervation in the Future Treatment of Resistant Hypertension?", Future Cardiology, 7(5): 591-594, 2011.

Mahfoud et al. "Renal Hemodynamics and Renal Function After Catheter-Based Renal Sympathetic Denervation in Patients With Resistant Hypertension", Hypertension, 60: 419-424, 2012.

Makris et al. "Resistant Hypertension Workup and Approach to Treatment", International Journal of Hypertension, 2011(Art. ID598694): 1-10, 2011.

Manasse et al. "Clinical Histopathology and Ultrstructural Analysis of Myocardium Following Microwave Energy Ablation", European Journal of Cardio-Thoracic Surgery, 23: 573-577, 2003.

Mangoni et al. "Effect of Sympathectomy on Mechanical Properties of Common Carotid and Femoral Arteries", Hypertension, 30: 1085-1088, 1997.

Martin et al. "Premise, Promise, and Potential Limitations of Invasive Devices to Treat Hypertension", Current Cardiology Reports, 13(1): 86-92, Feb. 2011.

Mazor "Efficacy of Renal Denervation Is Positively Impacted by Longitudinal Treatments", Vessix Vascular Inc., PowerPoint Presentation, TCT 2012, 20 P., 2012.

MERIT-HF Study Group "Effect of Metaprolol CR/XL in Chronic Heart Failure: Metoprolol CR/XL Randomised Intervention Trial in Congestive Heart Failure (MERIT-HF)", The Lancet, 353(9169): 2001-2007, Jun. 12, 1999.

Mogil et al. "Renal Innervation and Renin Activity in Salt Metabolism and Hypertension", American Journal of Physiology, 216(4): 693-697, Apr. 1969.

Moretti et al. "Beta Blocker for Patients With Pulmonary Arterial Hypertension: A Single Center Experience", International Journal of Cardiology, 184(1): 528-532, Available Online Feb. 24, 2015.

Mortensen et al. "Catheter-Based Renal Sympathetic Denervation Improves Central Hemodynamics and Arterial Stiffness: A Pilot Study", The Journal of Clinical Hypertension, 14(12): 861-870, Dec. 2012.

Nootens et al. "Neurohormonal Activation in Patients With Right Ventricular Failure From Pulmonary Hypertension: Relation to Hemodynamic Variables and Endothelin Levels", Journal of the American College of Cardiology, JACC, 26(7): 1581-1585, Dec. 1995.

Ohkubo et al. "Histological Findings After Angioplasty Using Conventional Balloon, Radiofrequency Thermal Balloon, and Stent for Experimental Aortic Coarctation", Pediatrics International, 46: 39-47, 2004.

Olafsson et al. "Ultrasound Current Source Density Imaging", IEEE Transactions on Biomedical Engineering, 55(7): 1840-1848, Jul. 2008.

Ong et al. "Successful Treatment of Resistant Hypertension With Percutaneous Renal Denervation Therapy", Heart, 98(23): 1754-1755, Dec. 2012.

Ormiston "OneShot (Covidien)", Maya Medical, Auckland, New Zealand, PowerPoint Presentation.

Ormiston et al. "First-in-Human Use of the OneShot™ Renal Denervation System From Covidien", EuroIntervention, 8: 1090-1094, 2013.

Packer et al. "Effect of Carvedilol on Survival in Severe Chronic Heart Failure", The New England Journal of Medicine, 344(22): 1651-1658, May 31, 2001.

Page et al. "The Effect of Renal Denervation on Patients Suffering From Nephritis", The Journal of Clinical Investigation, 14(4): 443-458, Jul. 1935.

Papademetriou et al. "Renal Sympathetic Denervation for the Treatment of Difficult-to-Control or Resistant Hypertension", International Journal of Hypertension, 2011(Art.ID196518): 1-8, Jan. 2011.

Para Tech Coating "Parylene Properties", Para Tech Coating Inc., 1 P., 2010.

Perros et al. "Nebivolol for Improving Endothelial Dysfunction, Pulmonary Vascular Remodeling, and Right Heart Function in Pulmonary Hypertension", Journal of the American College of Cardiology, JACC, 65(7): 668-680, Feb. 24, 2015.

Pokushalov et al. "A Randomized Comparison of Pulmonary Vein Isolation With Versus Without Concomitant Renal Artery Denervation in Patients With Refractory Symptomatic Atrial Fibrillation and Resistant Hypertension", Journal of the American College of Cardiology, 60(13): 1163-1170, 2012.

Prapa et al. "Histopathology of the Great Vessels in Patients With Pulmonary Arterial Hypertension in Association With Congenital Heart Disease: Large Pulmonary Arteries Matter Too", international Journal of Cardiology, 168: 2248-2254, Available Online Feb. 28, 2013.

Prochnau et al. "Catheter-Based Renal Denervation for Drug-Resistant Hypertension by Using A Standard Electrophysiology Catheter", EuroIntervention, 7: 1077-1080, 2012.

Prochnau et al. "Efficacy of Renal Denervation With A Standard EP Catheter in the 24-h Ambulatory Blood Pressure Monitoring—Long-Term Follow-Up", International Journal of Cardiology, 157(3): 447-448, Jun. 14, 2012.

Quinn "Pre-Eclampsia and Partial Uterine Denervation", Medical Hvpotheses, 64(3): 449-454, 2005. Abstract.

Rappaport "Treating Cardiac Disease With Catheter-Based Tissue Heating", IEEE Microwave Magazine, p. 57-64, Mar. 2002.

Reddy "Sound Intervention", Mount Sinai School of Medicine, MSSM, Presentation, 19 P., 2012.

Roehl et al. "Comparison of 3 Methods to Induce Acute Pulmonary Hypertension in Pigs", Comparative Medicine, 59(3): 280-286, Jun. 2009.

Rosanio et al. "Pulmonary Arterial Hypertension in Adults: Novel Drugs and Catheter Ablation Techniques Show Promise? Systematic Review on Pharmacotherapy and Interventional Strategies", BioMed Research International, XP055754039, 2014(1Art. 743868): 1-17, Jun. 12, 2014.

Rothman "FIM Evaluation of A New, Multi-Electrode RF System for Renal Denervation (Medtronic)", Medtronic Inc., PowerPoint Presentation, 8 P., 2012.

Rothman et al. "Pulmonary Artery Denervation Reduces Pulmonary Artery Pressure and Induces Histological Changes in An Acute Porcine Model of Pulmonary Hypertension", Circulation: Cardiovascular Interventions, 8(11): e002569-1-e002569-7, Published Online Nov. 17, 2015.

Rousselle "Experimental Pathways for the Evaluation of Extrinsic Renal Nerve Distribution, Density, and Quantification (Swine Model)", Alizee Pathology in Collaboration With Jack Skirkball Center for Cardiovascular Research, TCT, 20 P., Nov. 8, 2011.

Rousselle "Renal Artery Dervation: Experimental Pathways for the Evaluation of Extrinsic Renal Nerve Distribution, Density, and Quantification (Swine Model)", Alizee Pathology, Cardiovascular Research Foundation, Nov. 8, 2011.

Sakakura et al. "Methodological Standardization for the Pre-Clinical Evaluation of Renal Sympathetic Denervation", JACC: Cardiovascular Interventions. 7(10): 1184-1193, Published Online Sep. 14, 2014.

Sangiorgi et al. "Histo-Morphometric Evaluation of 2D Characteristics and 3D Sympatetic Renal Nerve Distribution in Hypertensive Vs. Normotensive Patients", Department of Pathology, Department of Cardiology, University of Rome Tor Vergata, Department of Cardiology University of Modena and Reggio Emilia, Medtronic Cardiovascular, PowerPoint Presentation, TCT 2012, 22 P., 2012.

Sanni et al. "Is Sympathectomy of Benefit in Critical Leg Ischaemia Not Amenable to Revascularisation?", Interactive Cardiovascular and Thoracic Surgery, 4: 478-483, 2005.

Scheinert "Cardiosonic TIVUS™ Technology: An Intra-Vascular Ultrasonic Catheter for Targeted Renal Denervation", Center for Vascular Medicine, Park Hospital Leipzig, Germany, PowerPoint Presentation, TCT 2012, 16 P., 2012.

Schelegle et al. "Vagal Afferents Contribute to Exacerbates Airway Responses Following Ozone and Allergen Challenge", Respiratory Physiology & Neurobiology, 181(3): 277-285, May 31, 2012.

(56) References Cited

OTHER PUBLICATIONS

Schlaich "Long-Term Follow Up of Catheter-Based Renal Denervation for Resistant Hypertension Confirms Durable Blood Pressure Reduction", Hypertension & Kidney Disease Laboratory, Baker IDI Heart & Diabetes Institute, Melbourne VIC, Australia, PowerPoint Presentation, TCT 2012, 22 P., 2012.
Schlaich et al. "Renal Sympathetic-Nerve Ablation for Uncontrolled Hypertension", New England Journal of Medicine, 361(9): 932-934, Aug. 27, 2009.
Schnyder et al. "Common Femoral Artery Anatomy Is Influenced by Demographics and Comorbidity: Implications for Cardiac and Peripherial Invasive Studies", Catheterization and Cardiovascular Interventions, 53(3): 289-295, Jul. 2001.
Schwartz "Strategies to Model Efficacy of Hypertension Devices", EuroPCR 2013, The Leading Cardiovascular Course, 24 P., 2013.
Shelton Jr. et al. "A Nondestructive Technique to Measure Pulmonary Artery Diameter and Its Pulsatile Variations", Journal of Applied Physiology, 33(4): 542-544, Oct. 1972.
Shung "Doppler Flow Measurements", Diagnostic Ultrasound—Imaging and Blood Flow Measurements, Chap.5:103-104, 2006.
Sievert et al. "Catheter-Based Technology Alternatives for Renal Denervation", Cardiovascular Center Frankfurt, Germany, TCT 2012, Miami, FL, USA, Oct. 22-26, 2012, PowerPoint Presentation, 35 P., Oct. 2012.
Simonneau et al. "Updated Clinical Classification of Pulmonary Hypertension", Journal of the American College of Cardiology, 54(1/Suppl.S): S43-S54, Jun. 30, 2009.
Sitbon et al. "Beyond A Single Pathway: Combination Therapy in Pulmonary Arterial Hypertension", European Respiratory Review, 25(142): 408-417, Dec. 2016.
SOLVD Investigators "Effect of Enalapril on Survival in Patients With Reduced Left Ventricular Ejection Fractions and Congestive Heart Failure", The New England Journal of Medicine, 325(5): 293-302, Aug. 1, 1991.
Souchon et al. "Monitoring the Formation of Thermal Lesions With Heat-Induced Echo-Strain Imaging: A Feasibility Study", Ultrasound in Medicine & Biology, 31(2): 251-259, 2005.
Stefanadis "Vincristine Local Delivery for Renal Artery Denervation", Athens, Greece, PowerPoint Presentation, TCT 2012, 21 P., 2012.
Steigerwald et al. "Morphological Assessment of Renal Arteries After Radiofrequency Catheter-Based Sympathetic Denervation in A Porcine Model", Journal of Hypertension, 30(11): 2230-2239, Nov. 2012.
Swierblewska et al. "An Independent Relationship Between Muscle Sympathetic Nerve Activity and Pulse Wave Velocity in Normal Humans", Journal of Hypertension, 28: 979-984, 2010.
Symplicity HTN-1 Investigators "Catheter-Based Renal Sympathetic Denervation for Resistant Hypertension: Durability of Blood Pressure Reduction Out to 24 Months", Hypertension, 57: 911-917, Mar. 14, 2011.
Symplicity HTN-2 Investigators "Renal Sympathetic Denervation in Patients With Treatment-Resistant Hypertension (The Symplicity HTN-2 Trial): A Randomised Controlled Trial", The Lancet, 376(9756): 1903-1909, Published Online Nov. 17, 2010.
Symplicity HTN-2 Investigators "Renal Sympathetic Denervation in Patients With Treatment-Resistant Hypertension (The Symplicity HTN-2 Trial): A Randomised Controlled Trial", The Lancet, 376: 1903-1909, Dec. 4, 2010.
Szabo "Diagnostic Ultrasound Imaging Inside Out", Academic Press Series in Biomedical Engineering, 2004.
Techavipoo et al. "Temperature Dependence of Ultrasonic Propagation Speed and Attenuation in Excised Canine Liver Tissue Measured Using Transmitted and Reflected Pulses", Journal of the Acoustical Society of America, 115(6): 2859-2865, Jun. 2004.
Thenappan et al. "Beta-Blocker Therapy Is Not Associated With Adverse Outcomes in Patients With Pulmonary Arterial Hypertension. A Propensity Score Analysis", Circulation Heart Failure, 7(6): 903-910, Published Online Oct. 2, 2014.

Tibshirani "Regression Shrinkage and Selction Via the Lasso: A Retrospective", Journal of the Royal Statistical Society, Series B: Statistical Methodology, 73(Pt.3): 273-282, 2011.
Tibshirani "Regression Shrinkage and Selection Via the Lasso", Journal of the Royal Statistical Society, Series B: Methodological, 58(1): 267-288, 1996.
Toorop et al. "Clinical Results of Carotid Denervation by Adventitial Stripping in Caotid Sinus Syndrome", Europan Journal of Vascular and Endovascular Syndrome, 39: 146-152, 2010.
Tyreus et al. "Two-Dimensional Acoustic Attenuation Mapping of High-Temperature Interstitial Ultrasound Lesions", Physics in Medicine and Biology, 49: 533-546, 2004.
Van Albada et al. "Biological Serum Markers in the Managment of Pediatric Pulmonary Arterial Hypertension", Pediatric Research, 63(3): 321-327, Mar. 2008.
Van Campen et al. "Bisoprolol in Idiopathic Pulmonary Arterial Hypertension: an Explorative Study", European Respiratory Journal, 48: 787-796, 2016.
Velez-Roa et al. "Increased Sympathetic Nerve Activity in Pulmonary Artery Hypertension", Circulation, 110(10): 1308-1312, Sep. 7, 2004.
Verloop et al. "The Effects of Renal Denervation on Renal Haemodynamics", Interventions for Hypertenison & Heart Failure, Abstracts of EuroPCR & AsiaPCR/SingLIVE 2013, May 21, 2013.
Virmani "Translation Medicine and Renal Denervation: Pre-Clinical Animal Models and Histoanatomy", CVPath Institute, Gaithersburg, MD, USA, PowerPoint Presentation.
Voskuil et al. "Percutaneous Renal Denervation for the Treatment of Resistant Essential Hypertension; The First Dutch Experience", Netherlands Heart Journal, 19(7-8): 319-323, Aug. 2011.
Warwick et al. "Trackless Lesions in Nervous Tissues Produced by High Intensity Focused Ultrsound (High-Frequency Mechanical Waves)", Journal of Anatomy, 102(3): 387-405, 1968.
Wikswo Jr. et al. "Magnetic Field of A Nerve Impulse: First Measurements", Science, 208: 53-55, Apr. 4, 1980.
Wilcox "Resistant Hypertension and the Role of the Sympathetic Nervous System", Medtronic, 30 P.
Williams et al. "Laser Energy Source in Surgical Atrial Fibrillation Ablation: Preclinical Experience", The Annals of Thoracic Surgery, 82: 2260-2264, 2006.
Witkowski "Future Perspective in Renal Denervation: Congestive Heart Failure, Insulin Resistance and Sleep Apnea", Innovations in Cardiovascular Interventions, ICI Meeting 2011, Tel Aviv, Israel, Dec. 4-6, 2011, 23 P., 2011.
Witkowski et al. "Effects of Renal Sympathetic Denervation on Blood Pressure, Sleep Apnea Course, and Glycemic Control in Patients With Resistant Hypertension and Sleep Apnea", Hypertension, 58(4): 559-565, Oct. 2011.
Witkowski et al. "Effects of Renal Sympathetic Denervation on Blood Pressure, Sleep Apnea Course, and Glycemic Control in Patients With Resistant Hypertension and Sleep Apnea", Hypertension, 58: 559-565, Aug. 15, 2011.
Witte et al. "Imaging Current Flow in Lobster Nerve Cord Using the Acoustoelectric Effect", Applied Physics Letters, 90: 163902-1-163902-3, 2007.
Wolf-De Jonge et al. "25 Years of Laser Assisted Vascular Anastomosis (LAVA): What Have We Learned?", European Journal of Vascular and Endovascular Surgery, 27(5): 466-476, May 2004.
Worthington et al. "Changes in Ultrasound Properties of Porcine Kidney Tissue During Heating", Ultrasound in Medicine & Biology, 27(5): 673-682, 2001.
Worthington et al. "Ultrasound Properties of Human Prostate Tissue During Heating", Ultrsound in Medicine & Biology, 28(10): 1311-1318, 2002.
Wright "On A Relationship Between the Arrhenius Parameters From Thermal Damage Studies", Transactions of the ASME, Technical Brief, Journal of Biomechanical Engineering, 125(2): 300-304, Apr. 9, 2003.
Wu et al. "A Quality Control Program for MR-Guided Focused Ultrasound Ablation Therapy", Journal of Applied Clinical Medical Physics, 3(2): 162-167, Spring 2002.

(56) References Cited

OTHER PUBLICATIONS

Wu et al. "Noninvasive Cardiac Arrhythmia Therapv Using High-Intensity Focused Ultrasound (HIFU) Ablation", International Journal of Cardiology, 166(2): e28-e30, Available Online Feb. 26, 2013.
Xu et al. "Experimental Nerve Thermal Injury", Brain, 117: 375-384, 1994.
Zeller "Percutaneous Renal Denervation System. The New Ultrasound Solution for the Mangament of Hypertension", Paradise Ultrasound Denervation System, ReCor Medical, 27 P., 2013.
Zhang et al. "Pulmonary Arterial Hypertension: Pharmacologic Therapies and Potential Pulmonary Artery Denervation Treatment", EuroIntervention, XP009524288, 9(Suppl.R): R149-R154, May 2013.
Zhou et al. "Pulmonary Artery Denervation Attenuates Pulmonarv Arterial Remodeling in Dogs With Pulmonary Arterial Hypertension Induced by Dehydrogenized Monocrotaline", JACC: Cardiovascular Interventions, 8(15): 2013-2023, Dec. 28, 2015.
Notice of Allowancedated Feb. 10, 2022 from U.S. Patent and Trademark Office Re. U.S. Appl. No. 13/905,224. (8 pages).
Official Action dated Jan. 21, 2022 From the U.S. Patent and Trademark Office Re. U.S. Appl. No. 16/451,087. (150 Pages).
Summons to Attend Oral Proceedings Pursuant to Rule 115(1) EPC dated Mar. 11, 2022 From the European Patent Office Re. Application No. 15862313.2. (12 Pages).

\* cited by examiner

| | Screening | Eligibility I | Eligibility II + Procedure (RHC)[5] | Hospital discharge | 2w ±5d | 1m± 1w | 6m± 1m | 12m ±1m | 24m ±3 m | 36m ±3 m | 48m ±3 m | 60m ±3 m |
|---|---|---|---|---|---|---|---|---|---|---|---|---|
| Informed consent | X | | | | | | | | | | | |
| Medical history/demographics | X | | | | | | | | | | | |
| Physical examination inc. vital signs and FC | X | X | X | X | X | X | X | X | | | | |
| Concomitant Medications | X | X | X | X | X | X | X | X | | | | |
| REVEAL Risk Score | | X | | | | | | | | | | |
| DLCO Test | | X | | | | | | | | | | |
| Serum pregnancy test (only if child bearing potential) | X | | X | | | | X | X | | | | |
| FBC, | | X | | X | | X | X | X | | | | |
| Liver enzyme | | X | | | | | X | X | | | | |
| Coagulation screen | | | X | | | | X | X | | | | |
| eGFR or serum creatinine | | X | | | | | X | X | | | | |
| 12 lead ECG | | X | | X | | | X | X | | | | |
| MRI | | X | | | | | X | X | | | | |
| Echocardiography | | X | | | | | X | X | X | X | X | X |
| 6MWD inc. Borg Dyspnea index, HR and O2 saturations | | X | | | | | X | X | X | | | |
| serum NT-pro-BNP | | X | | | | | X | X | X | | | |
| Right heart catheterization (RHC) | | | X | | | | X | X | | | | |
| Catecholamine Arterial vs. Venous | | | X | | | | X | X | | | | |
| Pulmonary artery denervation procedure | | | X | | | | | | | | | |
| Quality of life questionnaire | | X | | | | | X | X | | | | |
| Activity monitoring/actigraphy | | X | | | | | X | X | | | | |
| Adverse events | | X | X | X | X | X | X | X | | | | |
| Long term surveillance | | | | | | | | | X | X | X | X |

FIG. 1

| | Screening | Eligibility I | Eligibility II + Procedure (RHC)[5] | Hospital discharge | 2w[4] ±5d | 1m± 1w | 4m± 1m | 8m± 1m | 12m ±1m | 24m ±3 m | 36m ±3 m |
|---|---|---|---|---|---|---|---|---|---|---|---|
| Informed consent | x | | | | | | | | | | |
| Medical history/demographics | x[1] | | | | | | | | | | |
| Physical examination inc. vital sings and FC | x | x | x | x | x | x | x | x | x | | |
| Concomitant Medications | x | x | x | x | x | x | x | x | x | | |
| Serum pregnancy test (only if child bearing potential) | x | | x | | | x | x | | x | | |
| FBC, Liver enzyme | | x | | x | | x | x | x | x | | |
| Coagulation screen | | | x | | | | | x | x | | |
| eGFR or serum creatinine | | x | | | | x | x | | x | | |
| 12 lead ECG | | x | | x | | x | x | x | x | | |
| MRI/CT angiography | | x | | | | | x | | x | | |
| 6MWD Inc. Borg Dyspnea index, HR and 02 saturations | | x | | | | | x | x | x | | |
| serum NT-pro-BNP | | x | | x | | x | x | x | x | | |
| Right heart catheterization (RHC) | | | x | | | | | x | x | | |
| Catecholamine Arterial vs. Venous | | | x[2] | | | | | x | x | | |
| Pulomonary artery denervation procedure | | | x | | | | | | | | |
| Quality of life questionnaire | | x | | | | | | x | x | | |
| Activity monitoring/actigraphy | | x | | | | | | x | x | | |
| Adverse events | | x | x | x | x | x | x | x | x | | |
| Long term surveillance[3] | | | | | | | | | | x | x |

FIG. 3

PULMONARY HYPERTENSION TREATMENT

RELATED APPLICATIONS

This application is a National Phase of PCT Patent Application No. PCT/IL2018/050321 having International filing date of Mar. 20, 2018, which claims the benefit of priority under 35 USC § 119(e) of U.S. Provisional Patent Application Nos. 62/473,532, 62/473,545 and 62/473,512, all filed on Mar. 20, 2017. The contents of the above applications are all incorporated by reference as if fully set forth herein in their entirety.

PCT Patent Application No. PCT/IL2018/050321 is also related to PCT Patent Application No. PCT/IL2018/050322, entitled "PULMONARY HYPERTENSION TREATMENT METHOD AND/OR SYSTEM" of the same applicant, filed on Mar. 20, 2018.

PCT Patent Application No. PCT/IL2018/050321 is also related to PCT Patent Application No. PCT/IL2018/050316, entitled "METHOD FOR TREATING HEART FAILURE BY IMPROVING EJECTION FRACTION OF A PATIENT" of the same applicant, filed on Mar. 20, 2018.

FIELD AND BACKGROUND OF THE INVENTION

The present invention, in some embodiments thereof, relates to therapy, and more particularly, but not exclusively, to a treatment of pulmonary arterial hypertension.

Pulmonary arterial hypertension (PAH) generally involves the narrowing of blood vessels connected to and within the lungs, which may result in fibrosis of the blood vessels over time. As with other forms of pulmonary hypertension, the increased workload of the heart causes hypertrophy of the right ventricle, and ultimately right heart failure.

The following forms of PAH have been internationally recognized: idiopathic PAH; heritable PAH (associated with a BMPR2 mutation, with an ALK1 or endoglin mutation, or with an unknown cause); drug-induced and toxin-induced PAH; PAH associated with connective tissue disease, HIV infection, portal hypertension, congenital heart diseases, schistosomiasis or chronic hemolytic anemia; persistent pulmonary hypertension of the newborn; and pulmonary veno-occlusive disease (POVD) and/or pulmonary capillary hemangiomatosis (PCH) [Simonneau et al., *J Am Coll Cardiol* 2009, 54:S43-S54].

Current therapies in pulmonary arterial hypertension (PAH) target three separate signaling pathways: the prostaglandin pathway, endothelin pathway, and nitric oxide/guanylate cyclase pathway [Sitbon & Gaine, *Eur Respir Rev* 2016, 25:408-417; Galie et al., *Eur Heart J* 2016, 37:67-119].

Prostacyclin (prostaglandin $I_2$) is a potent vasodilator which induces relaxation of vascular smooth muscle, as well as being a potent inhibitor of platelet aggregation. Dysregulation of the prostacyclin metabolic pathway has been reported in patients with PAH.

Prostanoids (synthetic prostacyclin analogues) used in treatment of PAH include epoprostenol (synthetic prostacyclin) for intravenous administration; iloprost, for administration by inhalation or intravenous administration; beraprost, for oral administration; and treprostinil, for administration by inhalation, or oral, subcutaneous or intravenous administration.

Selexipag is an additional orally available drug for use in treating PAH. Selexipag and its active metabolite are selective prostacyclin receptor (IP) agonists. Although the mode of action of selexipag is similar to those of prostanoids, selexipag is chemically distinct from prostanoids and characterized by different pharmacology.

The endothelin (ET) system has an important role in the pathogenesis of PAH. Activation of the endothelin system has been reported in both plasma and lung tissue of PAH patients. Endothelin receptor antagonists used in treatment of PAH (especially mild to moderate PAH) include bosentan, ambrisentan, and macitentan. Ambrisentan is a selective inhibitor of type A endothelin receptor ($ET_A$), and bosentan and macitentan inhibit both type A ($ET_A$) and type B ($ET_B$) endothelin receptor.

Nitric oxide (NO) promotes vasodilation by activating soluble guanylate cyclase (sGC), an enzyme which synthesizes cyclic GMP (cGMP), a mediator of vasodilation.

Phosphodiesterase type-5 (PDE-5) inhibitors inhibit the breakdown of cyclic GMP (by PDE-5), thereby augmenting signaling downstream of nitric oxide, resulting in pulmonary vasodilation and anti-proliferation. PDE-5 inhibitors used for treatment of PAH include sildenafil, tadalafil and vardenafil.

Riociguat is a soluble guanylate-cyclase stimulator (sGCS), which increases sGC activity, thereby promoting vasodilation and inhibiting smooth muscle proliferation, leukocyte recruitment, platelet aggregation, and vascular remodeling. Riociguat is used to treat PAH and chronic thromboembolic pulmonary hypertension.

Sitbon & Gaine [*Eur Respir Rev* 2016, 25:408-417] and the 2015 European Society of Cardiology (ESC)/European Respiratory Society (ERS) Guidelines for the Diagnosis and Treatment of Pulmonary Hypertension [Galie et al., *Eur Heart J* 2016, 37:67-119] describe various combination therapies which target two or three of the abovementioned pathways, and which are recommended therein for treating PAH.

Chen et al. [*J Am Coll Cardiol* 2013, 62:1092-1100] report the use of pulmonary artery denervation using an ablation catheter to treat idiopathic PAH in human subjects. All subjects had received a diuretic and beraprost, with either sildenafil, bosentan or digoxin, and were identified as not responding optimally to therapy prior to denervation.

International Patent Application Publication WO 2016/084081 describes devices and methods for treating pulmonary hypertension, using a catheter device introduced to the pulmonary artery lumen to selectively modify nerve activity by emitting ultrasound energy.

Additional background art includes Galie & Manes [*J Am Coll Cardiol* 2013, 62:1101-1102], and U.S. Patent Application Publication No. 2013/0204068.

SUMMARY OF THE INVENTION

According to an aspect of some embodiments of the invention, there is provided a therapeutically active agent usable in the treatment of pulmonary arterial hypertension, for use in the treatment of pulmonary arterial hypertension in a subject in need thereof, wherein the treatment comprises administering the active agent to the subject and effecting pulmonary artery denervation in the subject.

According to an aspect of some embodiments of the invention, there is provided a method of treating pulmonary arterial hypertension in a subject in need thereof, the method comprising:

a) determining a responsiveness of the subject to at least one therapeutically active agent usable in treating pulmonary arterial hypertension; and b) effecting pulmonary artery denervation in a subject responsive to the at least one therapeutically active agent, thereby treating the pulmonary arterial hypertension.

According to an aspect of some embodiments of the invention, there is provided a method of treating pulmonary arterial hypertension in a subject in need thereof, the method comprising:

a) effecting pulmonary artery denervation in the subject; and b) administering to the subject at least one therapeutically active agent usable in treating pulmonary arterial hypertension, wherein the administering is at a sub-therapeutically effective amount, thereby treating the pulmonary arterial hypertension.

According to an aspect of some embodiments of the invention, there is provided a method of treating pulmonary arterial hypertension in a subject in need thereof, the method comprising effecting pulmonary artery denervation in the subject, the method being devoid of administering to the subject a therapeutically active agent usable in the treatment of pulmonary arterial hypertension for a time period of at least one month subsequent to the denervation, thereby treating the pulmonary arterial hypertension.

According to some of any of the embodiments of the invention, the at least one therapeutically active agent is selected from the group consisting of an anticoagulant, a prostacyclin receptor agonist, an endothelin inhibitor, and a guanylate cyclase activity enhancer.

According to some of any of the embodiments of the invention, the therapeutically active agent comprises a prostacyclin receptor agonist.

According to some of any of the embodiments of the invention relating to a therapeutically active agent which comprises prostacyclin receptor agonist, the at least one therapeutically active agent further comprises an endothelin inhibitor.

According to some of any of the embodiments of the invention relating to a therapeutically active agent which prostacyclin receptor agonist, the at least one therapeutically active agent further comprises a guanylate cyclase activity enhancer.

According to some of any of the embodiments of the invention relating to a treatment involving a prostacyclin receptor agonist, the treatment further comprises administering an endothelin inhibitor.

According to some of any of the embodiments of the invention relating to a treatment involving a prostacyclin receptor agonist, the treatment further comprises administering a guanylate cyclase activity enhancer.

According to some of any of the embodiments of the invention, the therapeutically active agent comprises an endothelin inhibitor.

According to some of any of the embodiments of the invention relating to a therapeutically active agent which comprises an endothelin inhibitor, the at least one therapeutically active agent further comprises a guanylate cyclase activity enhancer.

According to some of any of the embodiments of the invention relating to a treatment involving an endothelin inhibitor, the treatment further comprises administering a prostacyclin receptor agonist.

According to some of any of the embodiments of the invention relating to a treatment involving an endothelin inhibitor, the treatment further comprises administering a guanylate cyclase activity enhancer.

According to some of any of the embodiments of the invention, the therapeutically active agent comprises a guanylate cyclase activity enhancer.

According to some of any of the embodiments of the invention relating to a therapeutically active agent which comprises a guanylate cyclase activity enhancer, the at least one therapeutically active agent further comprises a prostacyclin receptor agonist.

According to some of any of the embodiments of the invention relating to a treatment involving a guanylate cyclase activity enhancer, the treatment further comprises administering a prostacyclin receptor agonist.

According to some of any of the embodiments of the invention relating to a treatment involving a guanylate cyclase activity enhancer, the treatment further comprises administering an endothelin inhibitor.

According to some of any of the embodiments of the invention, the therapeutically active agent comprises an anticoagulant.

According to some of any of the embodiments of the invention relating to a therapeutically active agent which comprises an anticoagulant, the at least one therapeutically active agent further comprises at least one therapeutically active agent selected from the group consisting of a prostacyclin receptor agonist, an endothelin inhibitor, and a guanylate cyclase activity enhancer.

According to some of any of the embodiments of the invention relating to a treatment involving an anticoagulant, the treatment further comprises administering at least one therapeutically active agent selected from the group consisting of a prostacyclin receptor agonist, an endothelin inhibitor, and a guanylate cyclase activity enhancer.

According to some of any of the embodiments of the invention, the anticoagulant is selected from the group consisting of warfarin, acenocoumarol, dicoumarol, ethylbiscoumacetate, phenprocoumon, tecarfarin, anisindione, fluindione, phenindione, atromentin, a heparin, fondaparinux, idraparinux, idrabiotaparinux, apixaban, betrixaban, darexaban, edoxaban, eribaxaban, letaxaban, otamixaban, rivaroxaban, hirudin, lepirudin, bivalirudin, desirudin, argatroban, inogatran, dabigatran, melagatran, ximelagatran, antithrombin, batroxobin, hementin, and vitamin E.

According to some of any of the embodiments of the invention, the prostacyclin receptor agonist is selected from the group consisting of prostacyclin (epoprostenol), iloprost, beraprost, treprostinil and selexipag.

According to some of any of the embodiments of the invention, the endothelin inhibitor comprises a selective $ET_A$ receptor antagonist, optionally ambrisentan.

According to some of any of the embodiments of the invention, the endothelin inhibitor comprises a dual $ET_A$/$ET_B$ receptor antagonist, optionally bosentan and/or macitentan.

According to some of any of the embodiments of the invention, the guanylate cyclase activity enhancer is selected from the group consisting of sildenafil, tadalafil, vardenafil and riociguat.

According to some of any of the embodiments of the invention relating to a treatment, the treatment comprises administering the active agent prior to and/or subsequent to the denervation.

According to some of any of the embodiments of the invention, the administering is of a therapeutically effective amount of the therapeutically active agent.

According to some of any of the embodiments of the invention relating to a treatment, the treatment comprises administering a sub-therapeutically effective amount of the therapeutically active agent subsequent to the denervation.

According to some of any of the embodiments of the invention relating to a treatment, the treatment comprises administering the active agent prior to the denervation, the treatment being devoid of administering the active agent for a time period of at least one month subsequent to the denervation.

According to some of any of the embodiments of the invention, the method or treatment described herein is devoid of administering to the subject the therapeutically active agent usable in the treatment of pulmonary arterial hypertension for a time period of at least one year subsequent to the denervation.

According to some of any of the embodiments of the invention relating to a sub-therapeutically effective amount, administering the sub-therapeutically effective amount comprises administering, subsequently to the denervation, a dosage of at least one therapeutically active agent which is lower than a dosage of the agent administered to the subject prior to the denervation.

According to some of any of the embodiments of the invention relating to a sub-therapeutically effective amount, administering the sub-therapeutically effective amount comprises administering, subsequently to the denervation, fewer therapeutically active agents than are administered to the subject prior to the denervation, wherein at least two therapeutically active agent usable in treating pulmonary arterial hypertension are administered to the subject prior to the denervation.

According to some of any of the embodiments of the invention, effecting the pulmonary artery denervation comprises thermally damaging nerve tissue associated with a main pulmonary artery.

According to some of any of the embodiments of the invention, thermally damaging nerve tissue comprises selectively damaging nerves that are not coated by myelin, by emitting energy at a frequency, intensity and duration sufficient to damage only nerves that are not coated by myelin, by producing a predetermined temperature profile in the treated tissue, the temperature profile ranging between 47-57° C.

According to some of any of the embodiments of the invention, thermally damaging nerve tissue is effected by cryotherapy and/or by emitting energy from at least one energy-emitting device introduced into the body.

According to some of any of the embodiments of the invention, the energy is selected from the group consisting of ultrasound energy and monopolar or bipolar radiofrequency energy.

According to some of any of the embodiments of the invention, the energy comprises unfocused ultrasound energy.

According to some of any of the embodiments of the invention, effecting the pulmonary artery denervation comprises introducing a catheter device comprising the at least one energy-emitting device into a main pulmonary artery lumen.

According to some of any of the embodiments of the invention, the energy-emitting device is a transceiver, and effecting the pulmonary artery denervation further comprises:

receiving, using the at least one energy-emitting transceiver, echo signals reflected from non-targeted tissue following emission of energy by the at least one transceiver;

analyzing the received echo signals to identify at least one of a type and location of the non-targeted tissue relative to the at least one transceiver; and emitting energy from the at least one transceiver in accordance with the analyzing, to modify nerve activity without substantially damaging the identified non-targeted tissue.

According to some of any of the embodiments of the invention, effecting the pulmonary artery denervation further comprises:

positioning the at least one energy-emitting device within the left pulmonary artery, right pulmonary artery and/or pulmonary artery trunk at a location which is in between the first bifurcation of the left pulmonary artery and the first bifurcation of the right pulmonary artery, wherein thermally damaging nerve tissue comprises emitting energy having parameters selected to damage nerves only within a distance window of between 0.2 mm and 10 mm from the intimal aspect of the pulmonary artery wall when the at least one device is positioned at the aforementioned location.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a table showing a protocol of a study for determining an effect of denervation in combination with drug therapy, according to some embodiments of the invention.

FIG. 3 is a table showing a protocol of a study for determining an effect of denervation in combination with drug therapy, according to some embodiments of the invention.

FIGS. 5A-5D present column charts showing changes in mean pulmonary arterial pressure (mPAP) (FIG. 5A), cardiac index (FIG. 5B), pulmonary vascular resistance (PVR)

(FIG. 5C), and right arterial pressure (RAP) (FIG. 5D), 4 months after denervation treatment according to some embodiments of the invention, in comparison with baseline levels.

Figure 6:
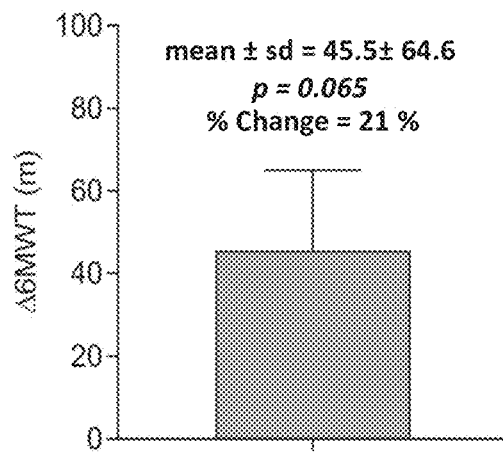

FIG. 6 is a column chart showing changes in 6-minute walking distance (6MWD) 4 months after denervation treatment according to some embodiments of the invention, in comparison with baseline levels.

Figure 7:
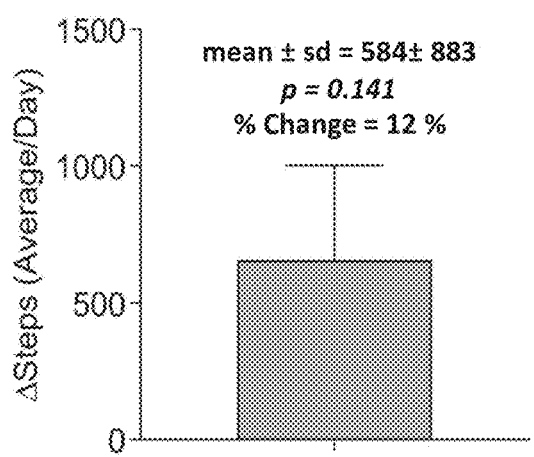

FIG. 7 is a column chart showing changes in activity, as determined by the number of steps detected by actigraphy, 4 months after denervation treatment according to some embodiments of the invention, in comparison with baseline levels.

Figure 8:
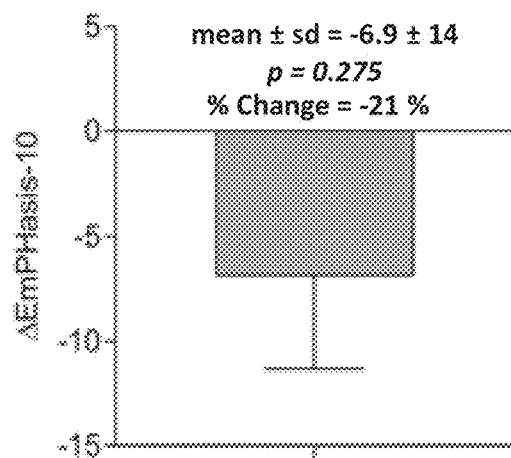

FIG. 8 is a column chart showing changes in quality of life, as determined by an emPHasis-10 questionnaire score 4 months after denervation treatment according to some embodiments of the invention, in comparison with baseline levels (lower score is associated with higher quality of life).

Figure 9:
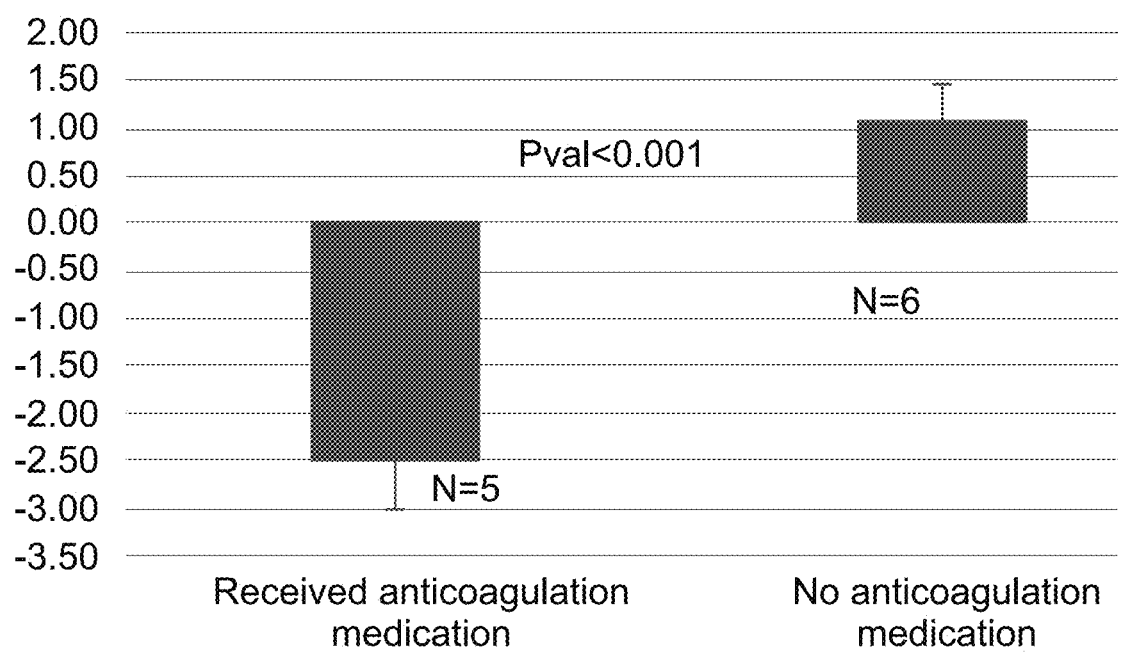

FIG. 9 is a column chart showing changes in pulmonary vascular resistance (PVR) in comparison with baseline levels 4 months after denervation treatment, in a group of patients receiving an anti-coagulation medication and in a group of patients that did not receive the anti-coagulation medication, according to some embodiments of the invention.

DESCRIPTION OF SPECIFIC EMBODIMENTS OF THE INVENTION

The present invention, in some embodiments thereof, relates to therapy, and more particularly, but not exclusively, to a treatment of pulmonary arterial hypertension.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

While investigating the effects of pulmonary artery denervation on pulmonary arterial hypertension, the present inventors have uncovered drug treatments which are particularly effective in combination with denervation.

The present inventors have further uncovered novel regimens for providing improved treatment of pulmonary arterial hypertension and/or for identifying subject populations with enhanced responsiveness to denervation.

While reducing the present invention to practice, the inventors have shown that denervation is effective in providing a considerable additional therapeutic effect in treating pulmonary arterial hypertension in subjects already undergoing drug therapy.

Without being bound by any particular theory, it is believed that drug treatment are particularly useful at targeting small distal pulmonary artery vessels, whereas denervation procedures are particularly useful at improving proximal pulmonary artery compliance, such that the drug administration and denervation procedures complement one another. It is further believed that the drug treatment influences vasodilation and remodeling processes, and the denervation reduces right ventricular afterload.

The inventors have further shown that subjects being treated (for pulmonary arterial hypertension) with anticoagulants are particularly responsive to denervation.

According to an aspect of some embodiments of the invention, there is provided a therapeutically active agent usable in the treatment of pulmonary arterial hypertension (PAH) (e.g., an agent according to any of the respective embodiments described herein), for use in the treatment of PAH in a subject in need thereof, wherein the treatment comprises administering the active agent to the subject and effecting pulmonary artery denervation (e.g., according to any of the respective embodiments described herein) in the subject.

According to an aspect of some embodiments of the invention, there is provided a use of a therapeutically active agent usable in the treatment of pulmonary arterial hypertension (PAH) (e.g., an agent according to any of the respective embodiments described herein) in the manufacture of a medicament for use in the treatment of PAH in a subject in need thereof, wherein the treatment comprises administering the active agent to the subject and effecting pulmonary artery denervation (e.g., according to any of the respective embodiments described herein) in the subject.

According to an aspect of some embodiments of the invention, there is provided a method of treating pulmonary arterial hypertension (PAH) in a subject in need thereof. The method comprises: a) effecting pulmonary artery denervation in the subject (e.g., according to any of the respective embodiments described herein); and b) administering to the subject at least one therapeutically active agent usable in the treatment of PAH (e.g., according to any of the respective embodiments described herein).

According to an aspect of some embodiments of the invention, there is provided a use of a device configured for effecting pulmonary artery denervation (e.g., according to any of the respective embodiments described herein) in the treatment of pulmonary arterial hypertension (PAH) in a subject in need thereof, wherein the treatment comprises administering at least one therapeutically active agent usable in the treatment of PAH (e.g., according to any of the respective embodiments described herein) and effecting pulmonary artery denervation in the subject.

Therapeutically Active Agent(s):

Examples of therapeutically active agents usable in the treatment of PAH (according to any one of the embodiments described herein) include, without limitation, anticoagulants, prostacyclin receptor agonists, endothelin inhibitors, and guanylate cyclase activity enhancers (as these terms are defined herein).

In some embodiments of any of the respective embodiments described herein, the therapeutically active agent comprises an anticoagulant. In some embodiments, denervation (e.g., according to any of the respective embodiments described herein) acts in synergy with an anticoagulant in treating pulmonary arterial hypertension.

In some embodiments of any of the respective embodiments described herein, the only therapeutically active agent utilized (according to any one of the embodiments described herein) is an anticoagulant.

In some embodiments of any of the respective embodiments described herein, an anticoagulant is utilized (according to any one of the embodiments described herein) in combination with an active agent other than an anticoagulant, for example, a prostacyclin receptor agonist, an endothelin inhibitor and/or a guanylate cyclase activity enhancer (e.g., according to any of the respective embodiments described herein).

Anticoagulants include, without limitation, vitamin K antagonists (e.g., coumarin derivatives and/or 1,3-inandione derivatives), heparin (optionally low molecular weight heparin) and derived substances, direct Xa inhibitors, direct thrombin inhibitors, antithrombin, batroxobin, hementin and vitamin E. In some embodiments of any of the embodiments described herein relating to an anticoagulant, the anticoagulant is a vitamin K antagonist, heparin or derived substance, direct Xa inhibitor, and/or direct thrombin inhibitor.

Examples of vitamin K antagonists include, without limitation, 4-hydroxycoumarin derivatives such as warfarin, acenocoumarol, dicoumarol, ethylbiscoumacetate, phenprocoumon and tecarfarin; 1,3-inandione derivatives such as anisindione, fluindione and phenindione; and atromentin. Warfarin, acenocoumarol and phenprocoumon are examples of relatively common vitamin K antagonists. Warfarin is an exemplary vitamin K antagonist.

Examples of heparins and derived substances include, for example, low molecular weight heparins such as bemiparin, nadroparin, reviparin, enoxaparin, parnaparin, certoparin, dalteparin and tinzeparin; and oligosaccharides such as fondaparinux, idraparinux and idrabiotaparinux. Enoxaparin and fondaparinux are exemplary anticoagulants which are a low molecular weight heparin or heparin-derived substance.

Examples of direct Xa inhibitors (which act directly on Factor X) include, without limitation, rivaroxaban, apixaban, betrixaban, darexaban, edoxaban, eribaxaban, letaxaban, and otamixaban. Rivaroxaban, apixaban, edoxaban and betrixaban are examples of relatively common direct Xa inhibitors. Rivaroxaban, apixaban and edoxaban are exemplary direct Xa inhibitors.

Examples of direct thrombin inhibitors (which directly inhibit thrombin) include, without limitation, bivalent direct thrombin inhibitors such as hirudin, bivalirudin, lepirudin and desirudin; and univalent direct thrombin inhibitors such as argatroban, inogatran, melagatran and dabigatran. Bivalirudin, lepirudin, desirudin, argatroban, and dabigatran are examples of relatively common direct thrombin inhibitors. Dabigatran is an exemplary direct thrombin inhibitor.

In some embodiments of any of the respective embodiments described herein, the anticoagulant is orally administrable. Examples of orally administrable anticoagulants include, without limitation, rivaroxaban, apixaban, edoxaban, betrixaban, dabigatran, and vitamin K antagonists which are 4-hydroxycoumarin or 1,3-inandione derivatives (according to any of the respective embodiments described herein).

In some embodiments of any of the respective embodiments described herein, the anticoagulant is intravenously and/or subcutaneously administrable, for example, administrable by IV (intravenous) pump and/or subcutaneous (SC) pump. Examples of intravenously and/or subcutaneously administrable prostacyclin receptor agonists include, without limitation, hirudin, bivalirudin, lepirudin, desirudin, batroxobin, and heparin and derived substances, according to any of the respective embodiments described herein.

In some embodiments of any of the respective embodiments described herein, a dosage of anticoagulant is sufficient to maintain an ACT (activated clotting time) higher than 270 seconds, for example, before, during and/or after a denervation treatment. In some embodiments, the ACT is higher than 275 seconds or higher than 280 seconds or any intermediate, smaller or larger value, for example, before, during and/or after a denervation treatment.

In some embodiments of any of the respective embodiments described herein, the therapeutically active agent comprises a prostacyclin receptor agonist. In some embodiments, denervation (e.g., according to any of the respective embodiments described herein) acts in synergy with a prostacyclin receptor agonist in treating pulmonary arterial hypertension.

In some embodiments of any of the respective embodiments described herein, the only therapeutically active agent utilized (according to any one of the embodiments described herein) is a prostacyclin receptor agonist.

In some embodiments of any of the respective embodiments described herein, a prostacyclin receptor agonist is utilized (according to any one of the embodiments described herein) in combination with an active agent other than a prostacyclin receptor agonist, for example, an anticoagulant, an endothelin inhibitor and/or a guanylate cyclase activity enhancer (e.g., according to any of the respective embodiments described herein).

Prostacyclin receptor agonists include prostacyclin (including epoprostenol) and prostacyclin analogues (also referred to as "prostanoids"), as well as agonists which are structurally unrelated to prostacyclin.

Examples of prostanoids include, without limitation, prostacyclin, AFP-07 (5Z-[(3aR,4R,5R,6aS)-3,3-difluorohexahydro-5-hydroxy-4-[(1E,3S,4S)-3-hydroxy-4-methyl-1-nonen-6-ynyl]-2H-cyclopenta[b]furan-2-ylidene]-pentanoic acid), alprostadil, beraprost, carbacyclin, cicaprost, iloprost, isocarbacyclin, taprostene, and treprostinil. Prostacyclin, iloprost, beraprost and treprostinil are examples of relatively common prostanoids.

Selexipag, ralinepag, ACT-333679 (a metabolite of selexipag), BMY-45778 ([3-(4,5-diphenyl[2,4'-bioxazol]-5'-yl) phenoxy] acetic acid) and TRA-418 ({4-[2-(1,1-diphenylethylsulfanyl)-ethyl]-3,4-dihydro-2H-benzo[1,4]oxazin-8-yloxy}-acetic acid) are non-limiting examples of a prostacyclin receptor agonist which is not a prostanoid. Selexipag is an example of a relatively common prostacyclin receptor agonist.

In some embodiments of any of the respective embodiments described herein, the prostacyclin receptor agonist is orally administrable. Examples of orally administrable prostacyclin receptor agonists include, without limitation, beraprost, treprostinil and selexipag.

In some embodiments of any of the respective embodiments described herein, the prostacyclin receptor agonist is administrable by inhalation. Examples of prostacyclin receptor agonists administrable by inhalation include, without limitation, treprostinil and iloprost.

In some embodiments of any of the respective embodiments described herein, the prostacyclin receptor agonist is intravenously administrable, for example, administrable by IV (intravenous) pump. Examples of intravenously administrable prostacyclin receptor agonists include, without limitation, prostacyclin, treprostinil, and iloprost.

In some embodiments of any of the respective embodiments described herein, the prostacyclin receptor agonist is subcutaneously administrable, for example, administrable by subcutaneous (SC) pump. Treprostinil is a non-limiting example of a subcutaneously administrable prostacyclin receptor agonist.

In some embodiments of any of the respective embodiments described herein, the therapeutically active agent comprises an endothelin inhibitor. In some embodiments, denervation (e.g., according to any of the respective embodiments described herein) acts in synergy with an endothelin inhibitor in treating pulmonary arterial hypertension.

In some embodiments of any of the respective embodiments described herein, the only therapeutically active agent utilized (according to any one of the embodiments described herein) is an endothelin inhibitor.

In some embodiments of any of the respective embodiments described herein, an endothelin inhibitor is utilized (according to any one of the embodiments described herein) in combination with an active agent other than an endothelin inhibitor, for example, an anticoagulant, a prostacyclin receptor agonist and/or a guanylate cyclase activity enhancer (e.g., according to any of the respective embodiments described herein).

Herein, the term "endothelin inhibitor" refers to an agent which inhibits a biological activity of an endothelin (e.g., endothelin-1, endothelin-2 and/or endothelin-3); for example, by interacting with an endothelin receptor (e.g., endothelin receptor antagonists) and/or by interacting with endothelin (e.g., by binding to endothelin) and/or by inhibiting endothelin secretion, as well as prodrugs of agents which exhibit such interactions.

In some embodiments of any of the respective embodiments described herein, the endothelin inhibitor is an endothelin receptor antagonist; optionally an antagonist of endothelin receptor type A ($ET_A$), endothelin receptor type B ($ET_B$) or both $ET_A$ and $ET_B$ (dual antagonists).

Examples of $ET_A$ receptor antagonists (e.g., selective antagonists) include, without limitation, ambrisentan, atrasentan, BQ-123, sitaxentan, and zibotentan. Ambrisentan is an example of an $ET_A$ antagonist particularly suitable for treating PAH, according to some embodiments.

Examples of dual antagonists of $ET_A/ET_B$ receptor include, without limitation, bosentan, macitentan and tezosentan. Bosentan and macitentan are examples of dual antagonists particularly suitable for treating PAH, according to some embodiments.

In some embodiments of any of the respective embodiments described herein, the therapeutically active agent comprises a guanylate cyclase activity enhancer. In some embodiments, denervation (e.g., according to any of the respective embodiments described herein) acts in synergy with a guanylate cyclase activity enhancer in treating pulmonary arterial hypertension.

In some embodiments of any of the respective embodiments described herein, the only therapeutically active agent utilized (according to any one of the embodiments described herein) is a guanylate cyclase activity enhancer.

In some embodiments of any of the respective embodiments described herein, a guanylate cyclase activity enhancer is utilized (according to any one of the embodiments described herein) in combination with an active agent other than a guanylate cyclase activity enhancer, for example, an anticoagulant, a prostacyclin receptor agonist and/or an endothelin inhibitor (e.g., according to any of the respective embodiments described herein).

Herein, the term "guanylate cyclase activity enhancer" refers to an agent which enhances a biological activity of guanylate cyclase; for example, by increasing a concentration of cyclic GMP (a compound formed by guanylate cyclase) by interacting with guanylate cyclase so as to increase cyclic GMP production (e.g., guanylate cyclase activators and/or stimulators) and/or by inhibiting breakdown of cyclic GMP (e.g., phosphodiesterase inhibitors), as well as prodrugs of agents which exhibit such interactions.

In some embodiments of any of the respective embodiments described herein, the guanylate cyclase activity enhancer is an inhibitor of phosphodiesterase 5 (a cyclic GMP-specific phosphodiesterase).

Examples of phosphodiesterase 5 (PDE5) inhibitors include, without limitation, avanafil, benzamidenafil, dasantafil, lodenafil, mirodenafil, sildenafil, tadalafil, vardenafil, udenafil, and zaprinast. Sildenafil, tadalafil and vardenafil are examples of PDE5 inhibitors particularly suitable for treating PAH, according to some embodiments.

In some embodiments of any of the respective embodiments described herein, the guanylate cyclase activity enhancer is an activator and/or stimulator of guanylate cyclase.

Examples of guanylate cyclase activators and/or stimulators include, without limitation, riociguat and cinaciguat. Riociguat is an example of a guanylate cyclase activity stimulator particularly suitable for treating PAH, according to some embodiments.

Regimen and/or Patient Population:

In some embodiments of any of the embodiments described herein relating to a treatment and/or method, the treatment and/or method comprises administering the active agent(s) (according to any of the respective embodiments described herein) prior to and/or subsequent to denervation (according to any of the respective embodiments described herein).

In some embodiments of any of the embodiments described herein relating to a treatment and/or method, the treatment and/or method comprises administering a therapeutically effective amount (as defined herein) of the therapeutically active agent (according to any of the respective embodiments described herein).

In some embodiments of any of the embodiments described herein relating to a treatment and/or method, the treatment and/or method comprises administering a sub-therapeutically effective amount (as defined herein) of the therapeutically active agent (according to any of the respective embodiments described herein), for example, subsequently to denervation (according to any of the respective embodiments described herein).

According to an aspect of some embodiments of the invention, there is provided a method of treating pulmonary arterial hypertension in a subject in need thereof, the method comprising: a) effecting pulmonary artery denervation; and b) administering to the subject at least one therapeutically active agent usable in treating pulmonary arterial hypertension, wherein the administering is at a sub-therapeutically effective amount (of the therapeutically active agent) and/or for a time period shorter than otherwise.

According to an aspect of some embodiments of the invention, there is provided a use of a device configured for effecting pulmonary artery denervation (e.g., according to any of the respective embodiments described herein) in the treatment of pulmonary arterial hypertension (PAH) in a subject in need thereof, wherein the treatment comprises administering to the subject at least one therapeutically active agent usable in the treatment of PAH (e.g., according to any of the respective embodiments described herein) at a sub-therapeutically effective amount and/or for a time period shorter than otherwise, and effecting pulmonary artery denervation in the subject.

Herein, the phrase "sub-therapeutically effective amount" refers to a dosage which is lower than a dosage (or dosage range) which is a therapeutically effective amount (as defined herein) in the absence of treatment by denervation.

The term "therapeutically effective amount" denotes a dosage of an active agent or a composition comprising the active agent that will provide the therapeutic effect for which the active agent is indicated, herein, treating pulmonary arterial hypertension (e.g., extending a life expectancy of subjects afflicted by pulmonary arterial hypertension).

In some embodiments of any of the embodiments described herein, according to any of the aspects described herein, a treatment and/or method comprises administering a sub-therapeutically effective amount (as defined herein) of an active agent subsequently to denervation, and administering a therapeutically effective amount (as defined herein) of the active agent prior to denervation (optionally only prior to denervation).

In some embodiments of any of the respective embodiments described herein, a sub-therapeutically effective amount is at least 25% lower than a therapeutically effective amount (e.g., the lower bound of a range of therapeutically effective amounts). In some such embodiments, the sub-therapeutically effective amount is at least 50% lower than a therapeutically effective amount.

Herein, the phrase "time period shorter than otherwise" refers to a duration of administration of an active agent which is shorter than a duration of administration of the active agent in the absence of treatment by denervation. Such a "shorter" time period may relate, for example, to cessation of administration (in a subject treated by denervation) at a time point during which administration would be continued in a subject not treated by denervation.

In some embodiments of any of the respective embodiments described herein, the subject is treated with at least two therapeutically active agents (according to any of the respective embodiments described herein), and the method comprises ceasing administration of at least one therapeutically active agent (such that administration of such an agent is for a time period shorter than otherwise) and continuing administration of at least one other therapeutically active agent (at a therapeutically effective amount and/or a sub-therapeutically effective amount, according to any of the respective embodiments described herein). In some such embodiments, ceasing administration of at least one therapeutically active agent is effected subsequent to denervation; optionally immediately subsequent to denervation (i.e., wherein the agent is not administered after denervation).

In some embodiments of any of the embodiments described herein relating to a treatment and/or method, the treatment and/or method comprises administering the active agent(s) (according to any of the respective embodiments described herein) prior to denervation (according to any of the respective embodiments described herein), and is devoid of administering the active agent for a time period of at least one month subsequent to the denervation (no agent is administered until after at least one month has elapsed from denervation). In some embodiments, the treatment and/or method is devoid of administering the active agent for a time period of at least three months subsequent to the denervation. In some embodiments, the treatment and/or method is devoid of administering the active agent for a time period of at least six months subsequent to the denervation. In some embodiments, the treatment and/or method is devoid of administering the active agent for a time period of at least one year subsequent to the denervation.

According to an aspect of some embodiments of the invention, there is provided a method of treating pulmonary arterial hypertension in a subject in need thereof, the method comprising effecting pulmonary artery denervation (according to any of the respective embodiments described herein) in the subject, the method being devoid of administering to the subject a therapeutically active agent usable in the treatment of PAH (according to any of the respective embodiments described herein) for a time period of at least one month subsequent to the denervation (no agent is administered until after at least one month has elapsed from denervation). In some embodiments, the method is devoid of administering the active agent for a time period of at least three months subsequent to the denervation. In some embodiments, the method is devoid of administering the active agent for a time period of at least six months subsequent to the denervation. In some embodiments, the method is devoid of administering the active agent for a time period of at least one year subsequent to the denervation.

Denervation may optionally be effected in a selected population of subjects, for example, based on observed correlations between responsiveness to active agents and responsiveness to denervation.

In some embodiments of any of the respective embodiments described herein, denervation is effected in a subject selected as being responsive to one or more therapeutically active agent.

In some embodiments of any of the respective embodiments described herein, the treatment comprises determining a responsiveness of the subject to one or more therapeutically active agent (according to any of the respective embodiments described herein).

In some embodiments of any of the respective embodiments described herein, the treatment comprises administering to a subject one or more therapeutically active agent (according to any of the respective embodiments described herein) during a first time period; determining a responsiveness of the subject to one or more therapeutically active agent (according to any of the respective embodiments described herein) administered during the first time period; and effecting denervation in a subject determined as being responsive to one or more therapeutically active agent administered during the first time period. In some such embodiments, the treatment is further characterized in that during a second time period subsequent to denervation, the treatment further comprises administering a sub-therapeutically effective amount of a therapeutically active agent (according to any of the embodiments described herein relating to a sub-therapeutically effective amount) and/or the treatment is devoid of administering a therapeutically active agent. In some embodiments, the second time period is at least one month (optionally at least one year) subsequent to the denervation (according to any of the respective embodiments described herein.

According to an aspect of some embodiments of the invention, there is provided a method of treating PAH in a subject in need thereof, the method comprising determining a responsiveness of the subject to one or more therapeutically active agent usable in treating PAH (according to any of the respective embodiments described herein). The method further comprises effecting pulmonary artery denervation (e.g., according to any of the embodiments described herein) in a subject responsive to the therapeutically active agent(s).

Responsiveness of a subject to a therapeutically active agent may be determined according to any suitable technique and/or criterion known in the art, for example, as described in the 2015 European Society of Cardiology (ESC)/European Respiratory Society (ERS) Guidelines for the Diagnosis and Treatment of Pulmonary Hypertension [Galie et al., *Eur Heart J* 2016, 37:67-119], the contents of which are incorporated herein by reference, especially contents regarding determining responsiveness (or lack thereof) of a treatment for PAH.

In some embodiments of any of the respective embodiments described herein, according to any of the aspects described herein, a subject responsive to a therapeutically active agent (e.g., as determined according to any of the respective embodiments described herein) achieves and/or maintains, upon treatment with the therapeutically active agent, at least one of the following features:

WHO functional class I or II (as defined in the art);
absence of progression of symptoms and clinical signs of right heart failure;
absence of syncope;
a six-minute walking distance (as defined and determined in the art) of over 440 meters; a peak $VO_2$—a.k.a. maximal oxygen consumption—(as determined by cardiopulmonary exercise testing) of over 15 ml per minute per kg and/or over 65% of the predicted peak $VO_2$ (e.g., according to sex, weight and/or height);

a $VE/VCO_2$ (ventilatory equivalents for $CO_2$) slope of less than 36;

BNP (brain natriuretic peptide) plasma levels of less than 50 ng/liter;

NT-proBNP (N-terminal prohormone of BNP) plasma levels of less than 300 ng/liter;

A right atrium (RA) area of less than 18 $cm^2$ with no pericardial effusion (as determined by echocardiography and/or cardiac magnetic resonance imaging);

a right atrial pressure (RAP) of less than 8 mmHg;

a cardiac index (CI) (as defined in the art) of at least 2.5 liters per minute per $meter^2$; and/or a mixed venous oxygen saturation ($SvO_2$) of over 65%.

Denervation:

Pulmonary artery denervation in the context of any of the embodiments described herein may optionally be effected according to any suitable denervation technique known in the art.

Herein and in the art, the term "denervation" refers to deprivation of an organ or body (e.g., an artery) from at least a portion of nerve supply, for example, by damaging and/or killing nerve cells.

Herein throughout, the phrase "pulmonary artery denervation" refers to denervation (as defined herein) of any one or more arteries in the pulmonary circulation system, including large arteries (e.g., the main pulmonary artery, including the right and left pulmonary arteries), small arteries, and arterioles.

In some embodiments of any of the embodiments described herein, pulmonary artery denervation comprises reducing nerve supply to pulmonary small arteries and/or arterioles.

In some embodiments of any of the embodiments described herein, pulmonary artery denervation comprises reducing sympathetic nerve supply to at least one artery in the pulmonary circulation system, for example, by damaging and/or killing sympathetic nerve cells innervating the artery. In some embodiments, pulmonary artery denervation comprises reducing sympathetic nerve supply to pulmonary small arteries and/or arterioles, for example, by damaging and/or killing sympathetic nerve cells innervating the small arteries and/or arterioles.

In some embodiments of any of the embodiments described herein, denervation comprises damaging nerve tissue (optionally killing nerve cells therein) in proximity to a main pulmonary artery. In some such embodiments, denervation is effected using a device (e.g., a catheter device) introduced into the main pulmonary artery (e.g., according to any of the respective embodiments described herein).

Herein, the phrase "main pulmonary artery" encompasses the pulmonary artery trunk, the right pulmonary artery (i.e., the right branch of the main pulmonary artery), and/or the left pulmonary artery (i.e., the left branch of the main pulmonary artery), including the bifurcation area of the pulmonary artery trunk.

It is to be appreciated that an artery deprived of nerve supply upon denervation is not necessarily an artery in proximity to nerve tissue damaged upon denervation. For example, damage to nerve tissue in proximity to a pulmonary artery trunk, right pulmonary artery, and/or left pulmonary artery may effect denervation of one or more small arteries and/or arterioles of the pulmonary circulation, which receive nerve supply from nerve cells which pass through a region in proximity to the pulmonary artery trunk, right pulmonary artery, and/or left pulmonary artery.

Denervation according to any one of the embodiments described herein may optionally be effected according to a technique described in International Patent Application Publication WO2016/084081, in Chen et al. [*J Am Coll Cardiol* 2013, 62:1092-1100], and/or in U.S. Patent Application Publication No. 2013/0204068; the contents of each of which are incorporated herein by reference in their entirety, and especially contents describing techniques for effecting denervation, and more especially contents describing denervation by emitting energy (e.g., ultrasound and/or electromagnetic radiation), for example, in accordance with any of the embodiments specifically described herein.

In some embodiments of any of the embodiments described herein, effecting denervation comprises thermally damaging nerve tissue surrounding the main pulmonary artery. Thermally damaging nerve tissue may optionally be effected by emitting energy (e.g., thereby heating the nerve tissue to a high temperature associated with tissue damage) and/or by cryotherapy (e.g., thereby cooling the nerve tissue to a low temperature associated with tissue damage).

In some embodiments of any of the embodiments described herein, effecting denervation by cryotherapy comprises introducing a catheter device into a main pulmonary artery lumen, wherein the catheter is configured to contain a low-temperature object.

In some embodiments of any of the embodiments described herein, effecting denervation comprises emitting energy from at least one energy-emitting device introduced into the body, for example, by introducing a catheter device comprising the energy-emitting device(s) into a main pulmonary artery lumen. The energy-emitting device(s) may optionally comprise a transmitter and/or a transceiver (e.g., an ultrasound transmitter and/or transceiver, and/or a radiofrequency transmitter and/or transceiver).

Emitted energy utilized for denervation (e.g., by thermally damaging nerve tissue) according to any of the respective embodiments described herein may optionally be ultrasound energy and/or electromagnetic radiation. Unfocused ultrasound energy is a non-limiting example of a suitable form of emitted ultrasound energy. Examples of suitable forms of emitted electromagnetic radiation include, without limitation, radiofrequency (RF) energy (monopolar or bipolar); microwave radiation; and ultraviolet, visible and/or infrared radiation (including, for example, phototherapy).

Additionally or alternatively, other forms of energy suitable to thermally damage nerve tissue are applied, such as plasma, mechanical manipulation, kinetic, nuclear, magnetic, electrical, potential, elastic mechanical, chemical and hydrodynamic energy.

In some embodiments, energy having parameters (e.g., intensity, frequency, beam shape, duration and/or other parameters) suitable to thermally damage nerve tissue is emitted. In some embodiments, parameters of the applied energy are selected in accordance with the anatomical treatment location, based on the type(s) and/or quantity and/or distribution of tissue that exist within the targeted volume. Optionally, selective treatment is performed, in which only a part of the tissue and/or a certain type of tissue within the target volume such as nerve tissue is affected by the emitted energy, while other tissue remains substantially unharmed. In an example, the applied energy parameters are selected to produce a temperature profile in the target tissue which thermally damages nerve tissue, but does not have a substantial effect (e.g., necrosis, denaturation) on non-targeted tissue within the target volume.

In some embodiments of any of the embodiments described herein, denervation of nerve tissue is effected within a predefined distance window from the main pulmonary artery wall. In some embodiments, the distance ranges between, for example, from 0.2 to 20 mm, 0.2 to 10 mm, 4 to 9 mm, 1 to 6 mm, or any intermediate, larger or smaller distance ranges relative to the intimal aspect of the artery wall. In some embodiments, a position of an energy-emitting devices (e.g., transceiver) and/or a catheter (according to any of the respective embodiments described herein) along the artery, and suitable energy parameters, are selected together in order to target nerve tissue within the predefined distance window. In some embodiments, one or more energy-emitting devices (e.g., transceivers), optionally of a catheter according to any of the respective embodiments described herein, are positioned within the main pulmonary artery (left pulmonary artery, right pulmonary artery and/or pulmonary artery trunk) within a limited area, in which the first bifurcation of the right pulmonary artery sets a border line and a first bifurcation of the left pulmonary artery sets a second border line. In some embodiments, an angiogram and/or CT and/or MRI images acquired before and/or during treatment are used for determining border line locations.

In some embodiments, the energy-emitting device(s) (e.g., transceiver(s)) are positioned such that a tissue volume covered by the beam of emitted energy encompasses mostly nerves innervating one or more arteries of the pulmonary circulation. Optionally, the volume is selected such that nerves innervating other organs are avoided or their presence is insignificant. Optionally, at least 25%, at least 50%, at least 60%, at least 70%, at least 80% by volume of nerve tissue within the tissue volume covered by the beam includes sympathetic nerves, or intermediate, higher or lower volume of nerve tissue.

In some embodiments, energy parameters are selected using a computational model that takes into account one or more of metabolic heat generation in tissue, heat absorption characteristics of the tissue, heat conductivity, metabolic flow in the tissue, tissue density, acoustic absorption, volumetric blood perfusion in the tissue, cell sensitivity to heat, cell sensitivity to mechanical or acoustical damage and/or other tissue parameters. In some embodiments, the model is constructed according to a finite element analysis which assists in determining a temperature distribution profile in the tissue, in space and/or time. Optionally, the finite element analysis takes into account a solution of the bioheat equation under selected conditions.

In some embodiments, the energy parameters are selected so that energy deposited in the tissue outside the artery is sufficient to thermally damage nerves within the distance window. In some embodiments, the emitted beam is selective in the sense that nerve tissue within the beam coverage is thermally damaged, while other, non-target tissue within the beam coverage (such as adipose tissue, lymph and/or other non-target tissue) remains substantially undamaged. In some embodiments, the tissue specific damage has a higher affinity to nerve tissue surrounded by fatty tissue, due to the low heat conductivity of the fatty tissue. Optionally, due to acoustic absorption and/or thermal sensitivity properties that are higher than acoustic absorption and/or thermal sensitivity properties of other tissue, such as lymph tissue, fibrous tissue, or connective tissue, the acoustic energy affects the nerve tissue most.

In some embodiments, cooling as a result of blood flow through the main pulmonary artery and/or cooling as a result of perfusion in the tissue reduces or prevents thermal damage to the intima and media layers of the artery wall, so that a significant thermal effect starts only at a distance away from the wall.

In some embodiments of any of the respective embodiments described herein, denervation comprises reducing thermal damage to the main pulmonary artery wall by taking advantage of a streaming effect produced in response to emission of ultrasound. In some embodiments, ultrasound emitted at a frequency of 8-13 MHz, 5-10 MHz, 10-20 MHz or intermediate, higher or lower frequency ranges and an intensity of from 20-100 W/cm$^2$, 30-70 W/cm$^2$, 35-65 W/cm$^2$, or intermediate, higher or lower intensity ranges produces fluid circulation in which fluid is caused to flow from the energy-emitting device surface towards the artery wall, thereby dissipating heat away from the ultrasound-emitting device (e.g., transceiver) and, in turn, from the artery wall. In some embodiments, even if fluid (e.g. blood) in the artery is static or the flow is reduced (e.g. due to pulsation, such as during diastole) the acoustic streaming effect produced by emission of ultrasound energy sufficiently cools the artery wall, preventing at least the intima and media of the artery wall from thermal damage. In some embodiments, cooling provided by the streaming effect is sufficient to dissipate at least 10%, at least 20%, at least 40% or intermediate, higher or lower percentage of the power of the emitted energy. In some embodiments, cooling provided by the streaming effect is sufficient to reduce a temperature of the intima to a temperature of 42° C. or lower.

In some embodiments of any of the embodiments described herein, denervation is performed at a plurality of locations situated along a long axis of the main pulmonary artery (left pulmonary artery, right pulmonary artery and/or pulmonary artery trunk), for example, from 2 to 8 locations within each of the left, right and main artery. According to some exemplary embodiments, denervation is performed at from 6 to 16 treatment locations, for example 6, 7, 8, 10, 12, 14 or any smaller or larger number of treatment locations within the pulmonary arteries. In some embodiments, the number of treatment locations within the pulmonary arteries is selected based on the anatomy of one or more of the pulmonary arteries and/or the distance from a selected nerve. In some embodiments, the number of treatment locations is selected based on the size of the "working frame", as described herein.

Optionally, a distance between adjacent treatment locations ranges from 0.1 to 2 cm, from 0.5 to 1 cm, from 1 to 2 cm, or intermediate, longer or shorter distances. In some embodiments, energy is emitted at plurality of locations to damage a nerve (or a bundle of nerves) at a plurality of sections along the length of the nerve. For example, a nerve may be damaged at an initial section of the axon and at a distal section of the axon (e.g., at or near the synapse), impairing also an intermediate section of the axon as a result. In some embodiments, the extent of thermal damage is high enough to prevent the nerve from reconnecting and/or regenerating for at least a time period following treatment (for example at least 1 month, 3 months, 6 months, 1 year following treatment). In some embodiments, nerve portions that transport, store and/or produce neurotransmitters are damaged.

In some embodiments, the catheter used for delivering the denervation has a length in a range of 80-200 cm, for example 80 cm, 100 cm, 120 cm or any intermediate, smaller or larger value.

According to some embodiments, denervation is effected for a duration in a range of 10-40 minutes, for example 15 minutes, 20 minutes, 25 minutes, 30 minutes or any intermediate, smaller or larger time duration. In some embodiments, the treatment duration is determined based on the number of selected treatment sites. Alternatively or additionally, the treatment duration is determined based on the distance between the treated nerve and the one or more treatment locations within the pulmonary arteries. Optionally, the treatment duration is determined based on the treatment protocol or parameters thereof.

In some embodiments of any of the respective embodiments described herein, thermal damage is manifested as coagulation, vacuolation and/or nuclei pyknosis of the targeted nerve. In some embodiments, the thermal damage results in tissue fibrosis and optionally in formation of remodeled scar tissue.

In some embodiments, a temperature distribution profile of the thermal damage produced depends on tissue homogeneity. Optionally, in homogenous tissue, a cross section profile of thermal damage takes the form of a teardrop.

In some embodiments of any of the respective embodiments described herein, denervation comprises thermally damaging nerve tissue (e.g., by emitting energy according to any of the respective embodiments described herein) without causing substantial damage to the artery wall. Optionally, damage to the wall is reduced by keeping the energy-emitting device(s) (e.g., ultrasound-emitting device(s)) according to any of the respective embodiments described herein away from the wall, for example by using a distancing device. In some embodiments, denervation comprises treating from an artery in which a wall disorder such as thrombus or atheroma exist, while reducing a risk of breakage of the thrombus or atheroma, which may result in emboli and possibly occlude the artery.

In some embodiments of any of the respective embodiments described herein, denervation comprises activating one or more energy-emitting devices (e.g., ultrasound-emitting devices) according to any of the respective embodiments described herein to emit energy towards a selected direction, and/or deactivating one or more energy-emitting devices (e.g., ultrasound-emitting devices) according to any of the respective embodiments described herein to reduce or prevent emission in one or more other directions.

In some embodiments of any of the respective embodiments described herein, thermally damaging nerve tissue associated with a pulmonary artery (e.g., a main pulmonary artery) comprises selectively damaging nerves that are not coated by myelin, for example, by subjecting the nerve tissue to a temperature at which nerves that are not coated by myelin are selectively damaged, optionally a temperature in a range of from 47° C. to 57° C. In some embodiments, selective damage of nerve tissue is effected by emitting energy (e.g., according to any of the embodiments described herein) at a frequency, intensity and/or duration sufficient to produce a suitable predetermined temperature profile in the tissue, for example, in a range of from 47° C. to 57° C. Optionally, upon increasing the temperature, for example, to a range of from 58° C. to 70° C., both non-coated nerves and myelin coated nerves are thermally damaged.

In some embodiments of any of the respective embodiments described herein, denervation comprises utilizing a transceiver, optionally an ultrasonic transceiver, as an energy-emitting device (according to any of the respective embodiments described herein), for example, to facilitate selective treatment of nerve tissue (e.g., causing damage to selected nerves without causing substantial damage to non-targeted tissue, such as surrounding organs and/or other nerve tissue). In some embodiments, denervation comprises using the same transceiver to characterize tissue and to emit energy for treating targeted tissue. In some embodiments, characterizing tissue comprises identifying one or more organs such as the lungs, trachea, lymph, bronchi or others. In some embodiments, organs are identified based on their echo signal reflection. Optionally, the reflected signals are received by the one or more ultrasonic transceivers (e.g., of a catheter device, according to any of the respective embodiments described herein), and are analyzed to determine the organ type and/or the relative distance of the organ from the lumen from which treatment is applied, such as the main pulmonary artery lumen. In some embodiments, the transceivers (e.g., ultrasonic transceivers) are activated at a first energy profile to identify and/or characterize tissue, and at a second energy profile to treat tissue. Optionally, non-targeted tissue is identified. Additionally or alternatively, targeted tissue is identified.

In some embodiments of any of the respective embodiments described herein, denervation comprises feedback-based treatment of the pulmonary vasculature. In some embodiments, treatment is continued and/or modified based on one or more measurements of physiological control parameters, including local parameters such as, for example, pulmonary artery diameter, bronchi diameter, and/or systemic parameters, which may be a byproduct of denervation, including, for example, heart rate, respiratory volume, and/or other physiological parameters. In some embodiments, the physiological parameters are measured internally to the body. Additionally or alternatively, the physiological parameters are measured externally to the body. In some embodiments, a catheter (e.g., ultrasonic catheter) according to any of the respective embodiments described herein is configured to acquire the one or more physiological parameters. In an example, a physiological parameter such as a diameter of the pulmonary artery is estimated by analyzing echo signals (e.g., ultrasound echo signals) reflected by the artery walls and received by the one or more transceivers (e.g., of a catheter device) according to any of the respective embodiments described herein. In some embodiments, the physiological parameter is acquired by stimulating the nervous system to evoke an observable physiological response and/or a chain of responses, one or more of which are detectable and optionally measureable.

In some embodiments, a measurement of the physiological parameter acquired before denervation treatment is compared to a measurement of the same physiological parameter following treatment, to determine treatment effectiveness. For example, an increase in artery diameter above a certain threshold, measured following treatment, may indicate that the treatment was effective.

In some embodiments, immediate feedback is provided, and denervation treatment is modified and/or ceased based on the feedback. In an example, immediate feedback comprises assessing dilation of the bronchi, which may be observed shortly after denervation. In another example, immediate feedback comprises assessing arterial blood pressure.

In some embodiments of any of the respective embodiments described herein, a catheter device (according to any of the respective embodiments described herein) introduced to a subject's body is suitable for reducing unwanted movement of the catheter, and more specifically movement of at least a distal portion of the catheter when a more proximal portion of the catheter is passed through cardiac vasculature, where it is subjected to movement resulting from heart pulsation. In some embodiments, the catheter is passed through the right ventricle of the heart. In some cases, contraction of the ventricle may cause movement of the catheter shaft, thereby possibly moving the distal head of the catheter, which comprises one or more energy-emitting devices according to any of the respective embodiments described herein).

In some embodiments, a structure of the catheter shaft is selected to damp movement resulting from heart pulsation, potentially reducing a number of movements and/or a range of movement of at least a distal head of the catheter. In some embodiments, one or more locations along the catheter shaft are structured to provide a full or partial axial decoupling between axial segments of the catheter, for example so that movement of the head at a distal end of the device is least affected by movement of a more proximal portion of the catheter shaft. Additionally or alternatively, the catheter is anchored to a certain location in the artery and/or to other tissue or organs, to prevent or reduce movement of the catheter relative to the tissue, for example during emission of energy, for example, ultrasound. Optionally, a small range of movement is permitted, such as movement to an extent which does not affect targeting. Additionally or alternatively, a "working frame" is provided, and the catheter is maneuvered within the working frame. Additionally or alternatively, movement of the catheter is synchronized with movement of the targeted tissue, for example by anchoring the catheter to a structure that moves in a similar pattern to the targeted tissue.

In some embodiments, at least a head of the catheter, comprising the one or more energy-emitting devices according to any of the respective embodiments described herein (ultrasound-emitting device(s)) is positioned and/or oriented within the lumen from which denervation treatment is applied at a predetermined location. Optionally, positioning of the catheter and/or directing of an energy (e.g., ultrasound) beam is selected based on one or more of: a distance from the tissue to be treated, a distance from the lumen wall, a position along the length of the lumen, parameters of the beam emitted by the energy-emitting devices (e.g., beam shape), and/or others. In some embodiments, positioning of the catheter and/or directing of the beam is performed by delivering the catheter over a pre-shaped guide wire, for example a spiral guide wire or a guide wire curved to a substantial Z shape. A potential advantage of the spiral configuration may include setting an advancement path for the catheter in which at any point along the path, at least the catheter head is maintained at a selected distance from the lumen wall, for example in proximity to the lumen wall. Optionally, the catheter is positioned a distance between 0.1 mm to 20 mm from the lumen wall. Optionally, the distance is selected in accordance with the intensity applied, for example a distance ranging from 0.1 mm to 5 mm, 5 mm to 10 mm, 15 mm to 20 mm or intermediate, larger or smaller distance ranges are used with an intensity between 20 $W/cm^2$ to 80 $W/cm^2$. In some embodiments, the spiral diameter (i.e. a diameter of a loop) is selected according to the lumen diameter. Additionally or alternatively, the spiral diameter is selected according to the catheter diameter, for example a diameter of the catheter head. In some embodiments, a similar effect to delivering the catheter over a helical structure may be obtained by delivering the catheter over the Z-shaped wire, and rotating the wire. Optionally, the catheter is introduced over the wire to a position in which the catheter head is proximal to the curved portion of the wire. Alternatively, the catheter is introduced over the wire to a position in which the catheter head is distal to the curved portion of the wire. Another potential advantage of the spiral and/or Z-shaped configurations (and/or any other configurations suitable to position the catheter away from the center of the lumen and in proximity to the walls) may include facilitating treating the lumen circumferentially. Optionally, when applying circumferential treatment by delivering the catheter over a curved guide wire, the curvature of the wire can be selected to obtain a certain orientation of the energy-emitting device(s) at the head of the catheter, for example positioning an energy-emitting device such that a longer dimension of the energy-emitting device (for example being a rectangular energy-emitting device) extends at an angle relative to a longitudinal axis of the lumen.

In some embodiments of any of the embodiments described herein, denervation relates to a selected target tissue volume. In some embodiments, denervation relates to an anatomical treatment zone for positioning an energy-emitting device according to any of the respective embodiments described herein (optionally an ultrasonic transceiver), optionally of a catheter according to any of the respective embodiments described herein, such that the emitting device is positioned to treat the aforementioned selected target tissue volume, while damage to non-targeted tissue types and/or non-targeted organs is reduced.

In some embodiments, the selected treatment zone (for denervation) provides for targeting a tissue volume comprising a high nerve content as compared to other tissue volumes, while reducing a risk of damage to non-targeted tissue (such as adipose tissue, connective tissue) and/or to nearby organs (such as the aorta, vagus, esophagus and/or other organs). A potential advantage of positioning an energy-emitting device and/or catheter at the selected treatment zone may include optimizing a tradeoff between denervation efficacy and treatment safety, such as avoiding damage to non-targeted tissue. Other optimization methods can include treating the most efficient treatment location. It was found to be the most efficient due to highest nerve density, and it is also, a safe location to treat.

In some embodiments, the anatomical treatment zone (for denervation) comprises an ostial and/or near-ostial area within the lumen of the left pulmonary artery, in the vicinity of the bifurcation in which the main pulmonary trunk splits into the left pulmonary artery and the right pulmonary artery. In some embodiments, the anatomical treatment zone is located at a distance of less than 50 mm, 40 mm, 30 mm, less than 20 mm, less than 10 mm, or intermediate, longer or shorter distances from a central longitudinal axis of the main trunk of the pulmonary artery. Additionally or alternatively, the anatomical treatment zone is situated at an axial distance (measured along the length of the left pulmonary artery) from 5 to 50 mm, 0 to 10 mm, 10 to 30 mm or intermediate, longer or shorter distance ranges from the artery ostium. Additionally or alternatively, the anatomical treatment zone is situated at a distance of less than 10 mm, less than 7 mm, less than 3 mm from the point of maximal curvature of the left pulmonary artery. Additionally or alternatively, the anatomical treatment zone is situated within the range of the first 1/5, 1/4, 1/3 or intermediate, longer or shorter sections of the total length of the left pulmonary artery, measured for example between the long axis of the main pulmonary trunk to the lateral bifurcation of the left pulmonary artery, where it splits into two or more branches, each extending towards one of the lobes of the left lung.

The "ostium" refers herein to the bifurcation point that is mutual to the main trunk, the left and the right pulmonary arteries.

In some embodiments the ostium point is first located by fluoroscopy prior to deciding the treatment zone for denervation.

In some embodiments, the anatomical treatment zone (for denervation) does not include the right pulmonary artery. A potential advantage of not treating from within the right pulmonary artery may include reducing potential damage (e.g. thermal damage) to the aorta, which ascends with the main pulmonary trunk and arches around the right pulmonary artery, and/or to reduce potential damage to the vagus nerve, which extends dorsally to the right pulmonary artery. Alternatively, the anatomical treatment zone comprises the right pulmonary artery.

In some embodiments, treatment for denervation (according to any of the respective embodiments described herein) is applied from the anatomical treatment zone to treat a selected target tissue volume. In some embodiments, the selected target tissue volume comprises one or more nerve plexuses situated to the left of the left pulmonary artery. In some embodiments, the selected target tissue volume is located laterally, posteriorly and/or anteriorly to the left pulmonary artery. In some embodiments, the selected target tissue volume is located within a distance range of 0.2-30 mm from a point of maximal curvature of the left pulmonary artery. Additionally or alternatively, the selected target tissue volume is located laterally to the main trunk of the pulmonary artery, inferior to the left pulmonary artery.

In some embodiments, energy is emitted towards a circumferential region of the left pulmonary artery. Optionally, the one or more energy-emitting devices (optionally ultrasound-emitting devices, e.g., transceivers) are activated and/or rotated during and/or between treatment sessions to cover different circumferential sections. In some embodiments, a line of energy-emitting devices (e.g., electrodes, ultrasonic transceivers) are aligned along the circumference of the artery and only the ones facing to target zone are activated. This may be potentially advantages to increasing safety.

In some embodiments, when emitting energy from the selected anatomical treatment zone towards the selected target tissue volume, a separation angle of at least 20 degrees, at least 30 degrees, at least 60 degrees or intermediate, larger or smaller angle is formed between the emitted energy beam and non-targeted organs. A potential advantage of emitting energy such that a separation angle is formed between the non-targeted organs and the emitted beam may include increasing treatment safety, as even if the beam is emitted at an offset angle from the selected angle, at least to some extent, non-targeted tissue will remain substantially unharmed.

In some embodiments, a structure of the catheter is designed to provide for positioning one or more energy-emitting devices (e.g., ultrasonic transceivers) within the anatomical treatment zone, for example by the catheter comprising a shaft that is shaped and/or deformable to a curvature that matches the curvature of the left pulmonary artery.

In some embodiments, denervation is effected using a catheter which exhibits synergy with the anatomy of the selected treatment zone and/or the anatomy of a delivery path of the catheter. In some embodiments, the physician utilizes the anatomy to direct the catheter to a selected treatment location, such as within the anatomical treatment zone described herein. In some embodiments, the anatomy naturally "assists" in directing the catheter to the selected location, for example by defining boundaries which force the catheter to the selected location.

In some embodiments, a shaft of the catheter is shaped in a manner in which at least some portions of the shaft lean and/or anchor against walls of a lumen through which the catheter is introduced to the selected treatment location, for example a lumen of the pulmonary artery trunk and/or a lumen of the right and/or left pulmonary arteries, to provide for positioning a head of the catheter at a selected treatment zone. In an example, the catheter shaft is arched, allowing a more proximal portion of the shaft to lean against a right wall of the pulmonary artery trunk to thereby position a more distal portion of the catheter which includes an energy-emitting device (or other device for effecting denervation) within a treatment zone located in the ostial left pulmonary artery section.

In some embodiments, a path through which an energy-emitting device and/or catheter is introduced to the treatment zone follows the natural path of blood flow. Optionally, the flow of blood assists in directing the energy-emitting device and/or catheter to the selected treatment location, for example by using an inflatable balloon tip and/or sail tip providing for flow-directed flotation of the energy-emitting device and/or catheter to the selected location.

In some embodiments of any of the embodiments described herein, denervation relates to targeting nerves according to mapping of the nerves. In some embodiments, nerves are selected as target according to one or both of a distance of the nerve from the artery lumen and a cross sectional area of the nerve. In some embodiments, a number of target nerves is selected to reduce one or more of: mPAP (mean pulmonary arterial pressure), pulmonary vascular resistance, contractibility, and/or systemic pressure levels in the pulmonary artery as compared to mPAP levels measured before treatment. In some embodiments, right heart ejection fraction is increased. Generally, the number of target nerves may be selected to improve (e.g. increase or decrease a level of) any parameter associated with pulmonary hypertension.

In some embodiments of any of the embodiments described herein, a catheter structure and/or a denervation protocol are selected based on an anatomy of the pulmonary artery region in which the catheter is intended to be positioned during treatment. For example, when positioning a catheter in the pulmonary artery trunk, in which the cross sectional area is relatively large (comprising a diameter which is about 1.5 times a diameter of the right or left pulmonary arteries), it may be desirable to position the catheter head closer to the lumen wall as compared to, for example, when treating in an artery region of smaller cross sectional area. Optionally, when treating an artery region having a relatively large cross sectional area, higher intensities are applied. In some embodiments, a high intensity is applied to compensate for undesired movement of the catheter within the large artery region. Optionally, by directing energy at a high intensity towards a large volume or cross section of tissue, the energy spreads over the large volume, thereby reducing the actual intensity of energy that effectively reaches the various tissue locations within the large volume.

In some embodiments of any of the embodiments described herein, denervation is effected (e.g., by selecting suitable parameters of energy emission) so as to reduce one or more of the following parameters: right atrial pressure (RAP), right ventricle pressures (RVP), systolic pulmonary artery pressure (sPAP), mean pulmonary artery pressures (mPAP), pulmonary vascular resistance (PVR), and/or NT-pro-BNP levels (e.g., as exemplified herein).

In some embodiments of any of the embodiments described herein, denervation is effected (e.g., by selecting suitable parameters of energy emission) so as to increase one or more of the following parameters: cardiac output (CO), cardiac index (CI), ejection fraction (EF), pulmonary distensability, pulmonary compliance, pulmonary stiffness, exercise tolerance—6 minutes walking distance (6MWD), quality of life (as assessed by questionnaire, e.g., emPHasis questionnaire), cardiopulmonary exercise testing and/or peak VO2 (e.g., as exemplified herein).

RAP, RVP, sPAP, mPAP, PVR, NT-pro-BNP levels, cardiac output, cardiac index, ejection fraction, pulmonary distensability, pulmonary compliance, pulmonary stiffness, exercise tolerance—6 minutes walking distance (6MWD), cardiopulmonary exercise testing and/or peak VO2 may be determined using any suitable technique, procedure, and/or apparatus known in the art (e.g., for cardiac MRI and/or echocardiography), optionally as described below in the Examples section herein and/or FIGS. 1 and/or 2.

Formulation:

The therapeutically active agent(s) of any of the embodiments of the invention described herein can be administered to a subject per se, or in a pharmaceutical composition where it is mixed with suitable carriers or excipients.

As used herein a "pharmaceutical composition" refers to a preparation of one or more of the active agents described herein with other chemical components such as physiologically suitable carriers and excipients. The purpose of a pharmaceutical composition is to facilitate administration of a compound to an organism.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active agent. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

Optionally, one may administer the pharmaceutical composition in a local rather than systemic manner, for example, via injection of the pharmaceutical composition directly into a tissue region (e.g., region of the vasculature) of a patient.

The term "tissue" refers to part of an organism consisting of cells designed to perform a function or functions. Examples include, but are not limited to, brain tissue, retina, skin tissue, hepatic tissue, pancreatic tissue, bone, cartilage, connective tissue, blood tissue, muscle tissue, cardiac tissue brain tissue, vascular tissue, renal tissue, pulmonary tissue, gonadal tissue, hematopoietic tissue.

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active agents into preparations which, can be used pharmaceutically. Proper formulation is dependent upon the route of administration chosen.

For injection, the active agents the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose; and/or physiologically acceptable polymers such as polyvinylpyrrolidone (PVP). If desired, disintegrating agents may be added, such as cross-linked polyvinylpyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin as well as soft, sealed capsules made of gelatin and a plasticizer, such as glycerol or sorbitol. The push-fit capsules may contain the active agents in admixture with filler such as lactose, binders such as starches, lubricants such as talc or magnesium stearate and, optionally, stabilizers. In soft capsules, the active agents may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active agents for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active agents may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active agents to allow for the preparation of highly concentrated solutions.

Alternatively, the active agent may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of some embodiments of the invention include compositions wherein the active agents are contained in an amount effective to achieve the intended purpose. More specifically, a therapeutically effective amount means an amount of active agent(s) effective to prevent, alleviate or ameliorate pulmonary arterial hypertension (or symptoms associated with pulmonary arterial hypertension), or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active agents described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. See e.g., Fingl, et al., 1975, in "The Pharmacological Basis of Therapeutics", Ch. 1 p. 1.

Dosage amount and interval may be adjusted individually to provide levels of the active agent(s) (e.g., in the blood) sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions according to some embodiments of the invention may, if desired, be presented in a pack or dispenser device, such as an FDA approved kit, which may contain one or more unit dosage forms containing the active agent(s). The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation according to the invention formulated in a compatible pharmaceutical carrier may also be prepared, placed in an appropriate container, and labeled for treatment of an indicated condition (e.g., in combination with pulmonary artery denervation), as is further detailed above.

As used herein the term "about" refers to ±20%, wherein in some embodiments of any of the respective embodiments described herein, "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

Safety and Effect of Denervation of Sympathetic Nerves in Combination with Drug Therapy on Pulmonary Arterial Hypertension The safety, performance and initial effectiveness of denervation of sympathetic nerves surrounding the pulmonary vasculature for treating PAH is evaluated. Denervation is effected using ultrasonic energy, optionally using a Therapeutic Intra-Vascular Ultra-Sound (TIVUS™) system.

Adult patients (e.g., about 15 patients) with idiopathic PAH, PAH associated with connective tissue disease, anorexigen-induced PAH and/or heritable PAH, are selected, in WHO functional class III (marked limitation of physical activity, comfortable at rest, less than ordinary activity causes undue dyspnoea or fatigue, chest pain or near syncope), with stable PAH on a stable drug regimen (i.e., with no changes of dose or medication for a minimum of 3 months prior to enrollment) of two PAH-specific medications other than parenteral prostanoids. The patients have eGFR levels of at least 30 ml per minute per 1.73 m$^2$ and/or serum creatinine levels of less than 150 µM.

PAH diagnosis is optionally confirmed by hemodynamic evaluation, which shows all of the following: mean pulmonary artery pressure (mPAP) of at least 25 mmHg at rest; pulmonary capillary wedge pressure (PCWP) or left ventricular end diastolic pressure (LVEDP) of no more than 15 mmHg; pulmonary vascular resistance (PVR) at rest of over 3 Wood units; and not meeting the criteria for a positive vasodilator response (fall in mPAP of at least 10 mmHg to no more than 40 mmHg).

Patients treated with parenteral prostanoids; patients having an implantable cardiac pacemaker, ICD, neurostimulator or drug infusion device; patients who have experienced a recent (e.g., in the previous 6 months) myocardial infarction, unstable angina pectoris or a cerebrovascular accident patients with a pulmonary artery aneurysm, moderate to severe pulmonary artery stenosis, significant co-morbid conditions and/or short life expectancy (e.g., less than a year); patients with pulmonary artery anatomy that precludes treatment or patients unable to undergo an MRI scan; and/or women who are pregnant or planning a pregnancy soon (e.g., within 12 months), are optionally excluded from the study.

Safety is determined by evaluating procedural related adverse events (complications) (e.g., up to 30 days post-procedure), including pulmonary artery perforation/dissection, acute thrombus formation in pulmonary artery, pulmonary artery aneurysm, vascular stenosis, hemoptysis, and/or death (including PAH-related and/or procedural related).

Safety is also optionally determined by evaluating long-term (e.g., up to 12 months post-procedure) procedural related adverse events (as described hereinabove), PAH worsening adverse events and/or death.

Variables which are determined in the course of the study include:

a) Changes from baseline of:

PAH-specific medications (e.g., at 2 weeks, 1 month, 6 months and/or 12 months);

Physical examination parameters (e.g., at 2 weeks, 1 month, 6 months and/or 12 months);

ECG (electrocardiography) parameters (e.g., at 1 month, 6 months and/or 12 months);

6-minute walking distance (6MWD) (e.g., at 1 month and/or 12 months);

Activity monitored using an actigraphy device (e.g., at 6 months and/or 12 months);

Arterial vs. venous catecholamine concentration (e.g., at 6 months and/or 12 months); and/or Hemodynamic response to inhaled nitric oxide, including mPAP and PVR (e.g., at 6 months and/or 12 months);

b) Cardiac and pulmonary MRI parameters (e.g., at 1 month);

c) Echocardiography parameters (e.g., at 12 months);

d) Quality of life, as determined by emPHasis questionnaire (e.g., at 12 months); and/or e) Long-term surveillance (e.g., at 2, 3, 4 and/or 5 years) for determining survival (or cause of mortality), hospitalization due to PAH, interventional or surgical procedures such as atrial septostomy or lung transplantation, worsening of WHO functional class, and/or escalation of drug therapy.

Figure 2:
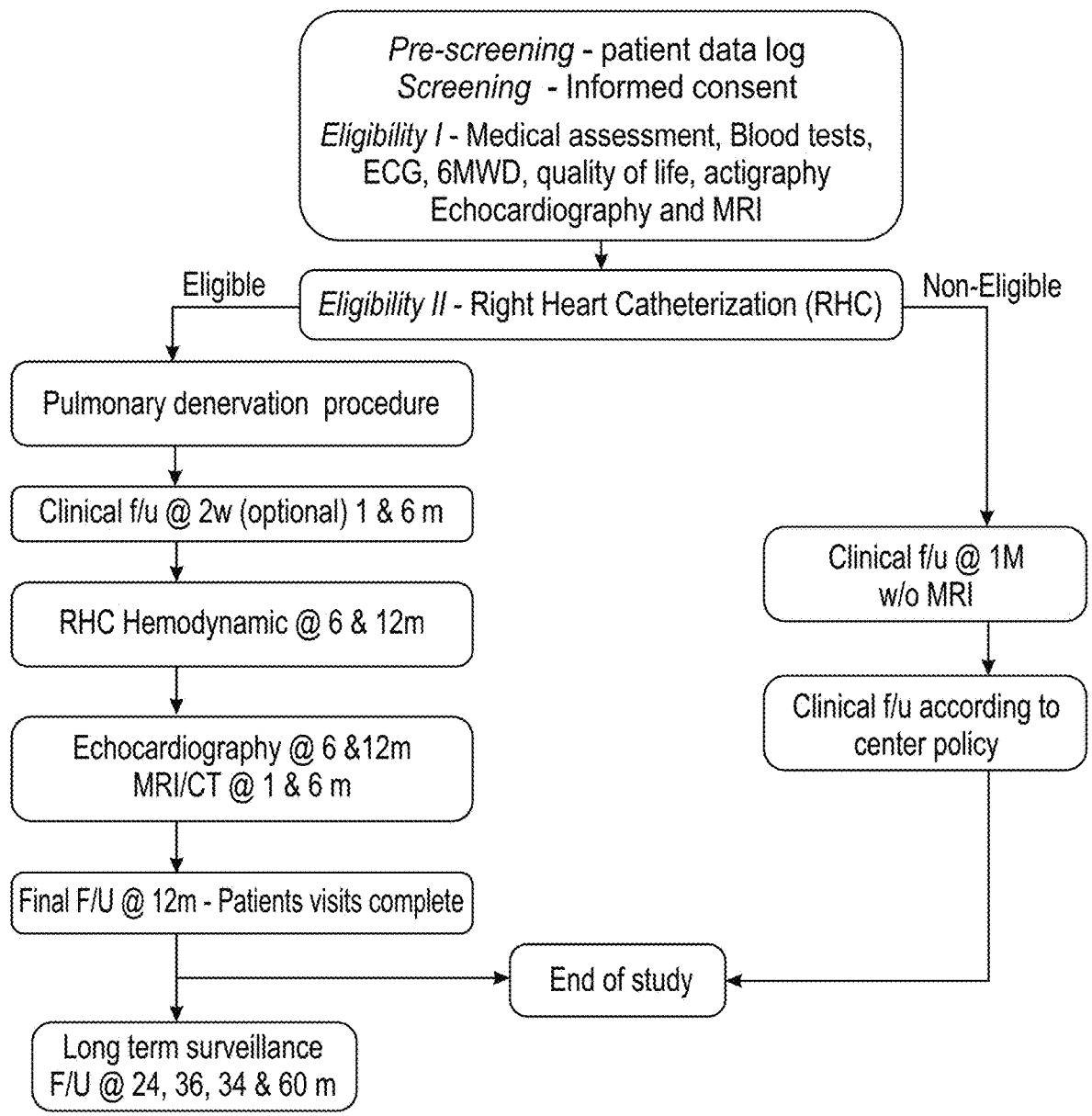
FIG. 2 is a flow chart for a protocol of a study for determining an effect of denervation in combination with drug therapy, according to some embodiments of the invention.

Elements of a study and optional times thereof are presented in FIG. 1. An optional flow chart for a study is presented in FIG. 2.

Effectiveness of treatment is determined by evaluating changes in hemodynamic changes from baseline (e.g., mPAP, PVR, right atrial pressure and/or cardiac index), change in 6MWD, change in quality of life, change in right ventricular (RV) function as assessed by MRI (e.g., RV ejection fraction, RV end diastolic and systolic volume, wall thickness, aortic flow, PA flow, and/or main, left and right PA diameter), change in right ventricular (RV) function/structure as assessed by echocardiography (e.g., tricuspid annular plane systolic excursion, RV myocardial performance index, RV ejection fraction, and/or RV end diastolic and systolic volume), and/or NT-pro BNP (N-terminal prohormone of brain natriuretic peptide) serum levels (e.g., at 1, 6 and/or 12 months).

Effectiveness of denervation in combination with any given drug therapy (e.g., combination of drugs) is optionally observed as improvement of patient condition in comparison with what would have been expected in the absence of denervation, e.g., based on baseline parameters, patient history, and/or expected progression of PAH as reported in the art.

Improvement of patient condition is optionally evidenced as a reduction one or more of: right atrial pressure (RAP), right ventricle pressures (RVP), systolic pulmonary artery pressure (sPAP), mean pulmonary artery pressures (mPAP), pulmonary vascular resistance (PVR), and/or NT-pro-BNP levels and/or as an increase in one or more of: cardiac output (CO), cardiac index (CI), ejection fraction (EF), pulmonary distensability, exercise tolerance—6 minutes walking distance (6MWD), quality of life (as assessed by questionnaire), cardiopulmonary exercise testing and/or peak VO2.

Comparison of results of different drug therapies (in combination with denervation) is optionally performed to determine a particularly effective drug or drug combination, in combination with denervation.

Example 2

Effect of Denervation of Sympathetic Nerves in Combination with Drug Therapy on Pulmonary Arterial Hypertension in Randomized Study The clinical effectiveness of denervation of sympathetic nerves surrounding the pulmonary vasculature in the treatment of PAH is evaluated using a randomized, single blind study. Denervation is effected using ultrasonic energy, optionally using a Therapeutic Intra-Vascular Ultra-Sound (TIVUS™) system, with some of the patients (e.g., about half) undergoing a sham treatment with the ultrasonic system, as a control group.

Adult patients (e.g., about 120 patients) with idiopathic PAH, PAH associated with connective tissue disease, anorexigen-induced PAH and/or heritable PAH, are selected according to the criteria described hereinabove, on a stable drug regimen (as defined hereinabove) of at least two PAH-specific medications. Variables which are determined in the course of the study (in comparison with baseline values) include:

a) Cardiac MRI parameters relating to right ventricular (RV) function (e.g., at 6 and/or 12 months);

b) Peak $VO_2$ as evaluated by CPET (cardiopulmonary exercise testing) (e.g., at 6 and/or 12 months);

c) NT-pro BNP (N-terminal prohormone of brain natriuretic peptide) serum levels (e.g., at 6 and/or 12 months);

d) Activity monitored using an actigraphy device (e.g., at 6 and/or 12 months);

e) Quality of life, as determined by emPHasis questionnaire (e.g., at 6 and/or 12 months); and/or f) Long-term surveillance (e.g., at 2 and/or 3 years) for determining survival (or cause of mortality), hospitalization due to PAH, interventional or surgical procedures such as atrial septostomy or lung transplantation, worsening of WHO functional class, and/or escalation of drug therapy.

Safety is optionally evaluated as described hereinabove (e.g., at up to 12 months post-procedure).

Effectiveness of treatment is determined by evaluating change in right ventricular (RV) function as assessed by MRI (e.g., RV ejection fraction, RV end diastolic and systolic volume, wall thickness, aortic flow, PA flow, and/or main, left and right PA diameter), change in peak $VO_2$, activity measured (e.g., by actigraphy) as steps per awake hours, change in quality of life, and/or NT-pro BNP serum levels.

Effectiveness of denervation in combination with any given drug therapy (e.g., combination of drugs) is optionally observed as improved patient condition in denervation-treated group relative to sham treatment.

Improvement of patient condition is optionally evidenced as a reduction one or more of: right atrial pressure (RAP), right ventricle pressures (RVP), systolic pulmonary artery pressure (sPAP), mean pulmonary artery pressures (mPAP), pulmonary vascular resistance (PVR), and/or NT-pro-BNP levels and/or as an increase in one or more of: cardiac output (CO), cardiac index (CI), ejection fraction (EF), pulmonary distensability, exercise tolerance—6 minutes walking distance (6MWD), quality of life (as assessed by questionnaire), cardiopulmonary exercise testing and/or peak VO2.

Comparison of results of different drug therapies (in combination with denervation) is optionally performed to determine a particularly effective drug or drug combination, in combination with denervation.

Example 3

Figure 4:
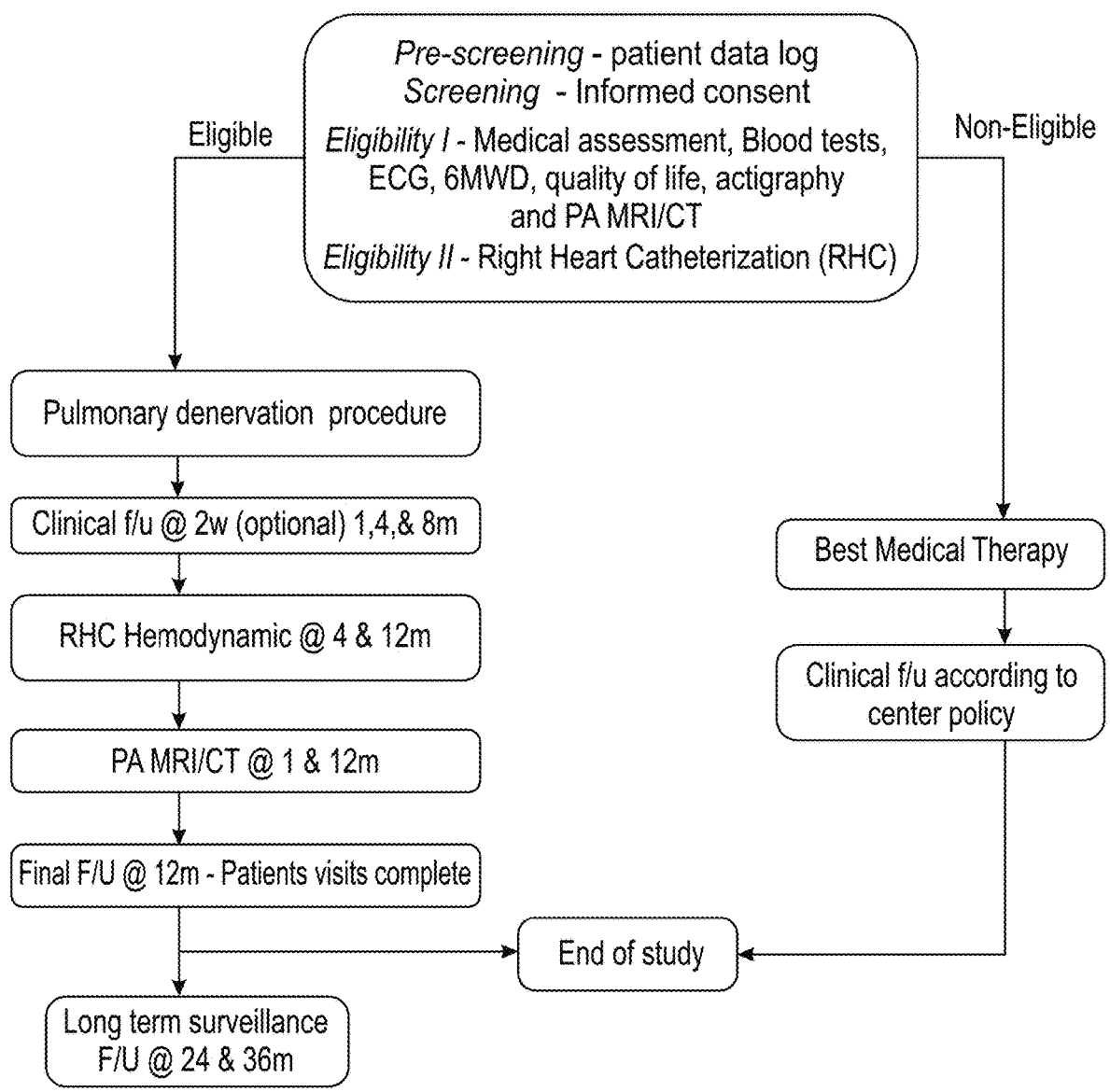
FIG. 4 is a flow chart for a protocol of a study for determining an effect of denervation in combination with drug therapy, according to some embodiments of the invention.
Figure 5A:
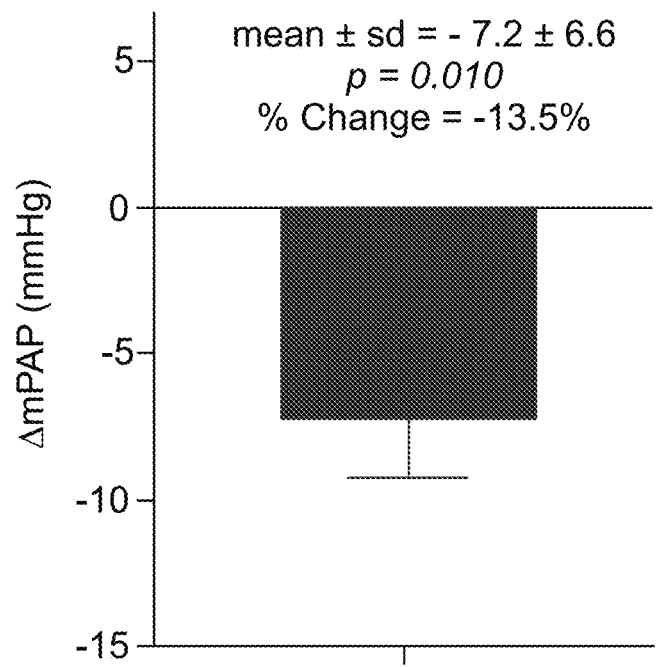
Figure 5B:
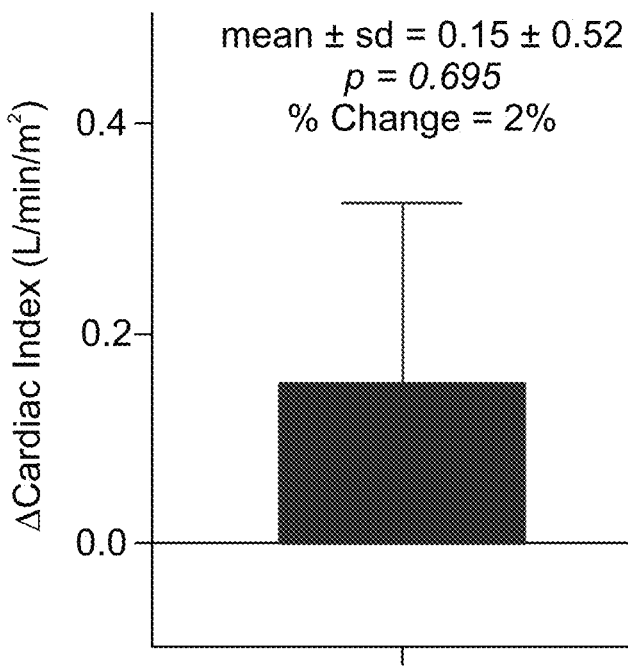
Figure 5C:
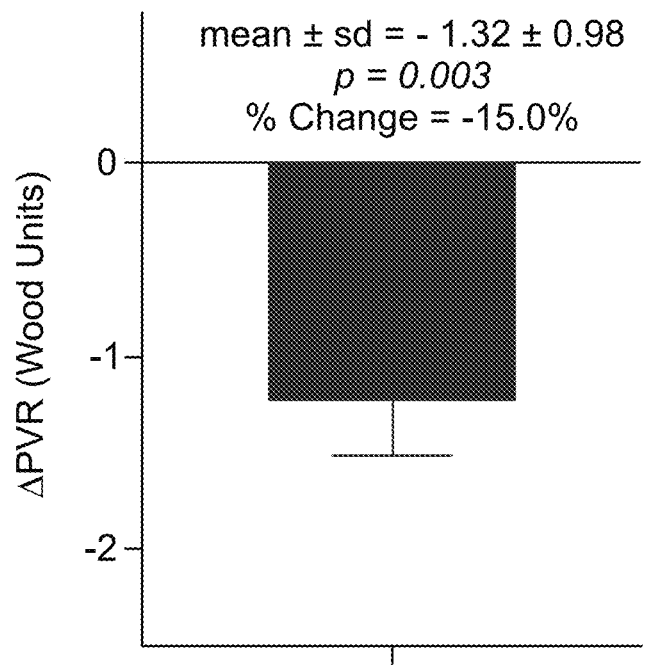
Figure 5D:
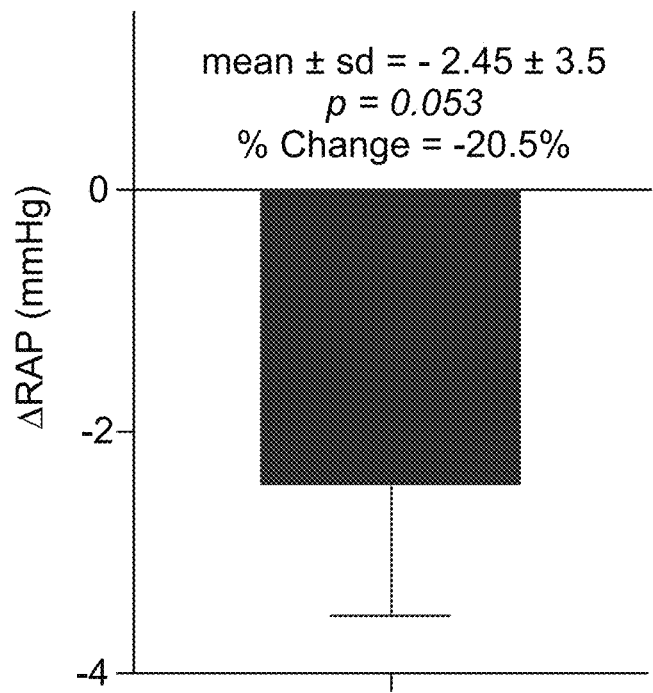

Safety and Effect of Denervation of Sympathetic Nerves in Combination with Drug Therapy on Pulmonary Arterial Hypertension The safety, performance and initial effectiveness of denervation of sympathetic nerves surrounding the pulmonary vasculature for treating PAH was evaluated according to procedures similar to those described in Example 1. Elements of a study are presented in FIG. 3. A flow chart for a study is presented in FIG. 4.

Denervation was effected using ultrasonic energy, using a Therapeutic Intra-Vascular Ultra-Sound (TIVUS™) system.

14 adult patients with PAH in WHO functional class II-III were tested, with stable PAH on a stable drug regimen (i.e., with no changes of dose or medication for a minimum of 3 months prior to enrollment) of two PAH-specific medications other than parenteral prostanoids.

The denervation procedure lasted 20-30 minutes on average, usability feedback from the operators was excellent, and no severe adverse events were recorded at 1, 4, 8 and 12 month follow-up; indicating that denervation using a TIVUS™ system is an easy to perform, straightforward, predictable and safe procedure. The number of denervation sites for each patient ranged from 6 to 16, according to patient anatomy.

11 of the patients continued their drug regimens for at least 4 months after treatment, at which time the following were determined:

Hemodynamic changes from baseline, for mPAP, PVR, right atrial pressure and cardiac index;

6-minute walking distance (6MWD);

Activity monitored using an actigraphy device; and

Quality of life, as determined by emPHasis-10 questionnaire (2 patients who did not complete 4 months of drug regimen were also included in quality of life analysis).

As shown in FIGS. 5A-5D, hemodynamic parameters were consistently improved 4 months after denervation treatment in subjects undergoing drug therapy for PAH, with mean pulmonary arterial pressure (mPAP) being reduced by an average of about 14% (FIG. 5A), cardiac index values being increased by an average of about 2% (FIG. 5B), pulmonary vascular resistance (PVR) values being reduced by an average of about 15% (FIG. 5C), and right atrial pressure being reduced by an average of about 20% (FIG. 5D), relative to baseline.

In addition, as shown in FIG. 6, 6-minute walking distance (6MWD) increased by an average of about 21% relative to baseline, 4 months after denervation treatment in subjects undergoing drug therapy for PAH.

As shown in FIG. 7, subject activity (as determined by actigraphy) increased by an average of about 12% relative to baseline, 4 months after denervation treatment in subjects undergoing drug therapy for PAH.

As shown in FIG. 8, subject emPHasis-10 questionnaire scores decreased by an average of about 21% relative to baseline, indicating an increase of quality of life.

The above results, showing improvement in subjects on a stable drug therapy, indicate that denervation complements drug therapy of PAH, suggesting that denervation exhibit beneficial effects via a different mechanism than do therapeutically active agents for PAH.

As shown in FIG. 9, pulmonary vascular resistance (PVR) were reduced 4 months after denervation in subjects treated by an anticoagulant (warfarin, rivaroxaban, dabigatran, apixaban, edoxaban, enoxaparin and/or fondaparinux), but not in subjects not treated regularly by an anticoagulant.

This result indicates that denervation is particularly suitable for use in treating PAH in combination with anticoagulants, for example, in a subpopulation of subjects who are treated by anticoagulants.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating pulmonary arterial hypertension in a subject in need thereof, the method comprising:
    a) determining a responsiveness of the subject to at least one anticoagulant usable in treating pulmonary arterial hypertension; and
    b) effecting pulmonary artery denervation in a subject responsive to said at least one anticoagulant,
    thereby treating the pulmonary arterial hypertension.

2. The method of claim 1, wherein said anticoagulant is selected from the group consisting of warfarin, acenocoumarol, dicoumarol, ethylbiscoumacetate, phenprocoumon, tecarfarin, anisindione, fluindione, phenindione, atromentin, a heparin, fondaparinux, idraparinux, idrabiotaparinux, apixaban, betrixaban, darexaban, edoxaban, eribaxaban, letaxaban, otamixaban, rivaroxaban, hirudin, lepirudin, bivalirudin, desirudin, argatroban, inogatran, dabigatran, melagatran, ximelagatran, antithrombin, batroxobin, hementin, and vitamin E.

3. The method of claim 1, wherein effecting said pulmonary artery denervation comprises thermally damaging nerve tissue associated with a main pulmonary artery.

4. The method according to claim 3, wherein said thermally damaging nerve tissue comprises selectively damaging nerves that are not coated by myelin, by emitting energy at a frequency, intensity and duration sufficient to damage only nerves that are not coated by myelin, by producing a predetermined temperature profile in the treated tissue, said temperature profile ranging between 47-57° C.

5. The method according to claim 3, wherein said thermally damaging nerve tissue is effected by cryotherapy and/or by emitting energy from at least one energy-emitting device introduced into the body.

6. The method according to claim 5, wherein said energy is selected from the group consisting of ultrasound energy and monopolar or bipolar radiofrequency energy.

7. The method according to claim 6, wherein said energy comprises unfocused ultrasound energy.

8. The method according to claim 5, wherein effecting said pulmonary artery denervation comprises introducing a catheter device comprising said at least one energy-emitting device into a main pulmonary artery lumen.

9. The method according to claim 5, wherein said energy-emitting device is a transceiver, and effecting said pulmonary artery denervation further comprises:
    receiving, using said at least one energy-emitting transceiver, echo signals reflected from non-targeted tissue following emission of energy by said at least one transceiver;
    analyzing said received echo signals to identify at least one of a type and location of said non-targeted tissue relative to said at least one transceiver; and
    emitting energy from said at least one transceiver in accordance with said analyzing, to modify nerve activity without substantially damaging said identified non-targeted tissue.

10. The method according to claim 5, wherein effecting said pulmonary artery denervation further comprises:
    positioning said at least one energy-emitting device within the left pulmonary artery, right pulmonary artery and/or pulmonary artery trunk at a location which is in between the first bifurcation of the left pulmonary artery and the first bifurcation of the right pulmonary artery,
    wherein said thermally damaging nerve tissue comprises emitting energy having parameters selected to damage nerves only within a distance window of between 0.2 mm and 10 mm from the intimal aspect of the pulmonary artery wall when said at least one device is positioned at said location.

11. The method of claim 1, wherein said anticoagulant is selected from the group consisting of warfarin, acenocoumarol, dicoumarol, ethylbiscoumacetate, phenprocoumon, tecarfarin, anisindione, fluindione, phenindione, and atromentin.

12. The method of claim 1, wherein said anticoagulant is selected from the group consisting of bemiparin, nadroparin, reviparin, enoxaparin, parnaparin, certoparin, dalteparin, tinzeparin, fondaparinux, idraparinux, and idrabiotaparinux.

13. The method of claim 1, wherein said anticoagulant is selected from the group consisting of rivaroxaban, apixaban, betrixaban, darexaban, edoxaban, eribaxaban, letaxaban, and otamixaban.

14. The method of claim 1, wherein said anticoagulant is selected from the group consisting of hirudin, bivalirudin, lepirudin, desirudin, argatroban, inogatran, melagatran, and dabigatran.

* * * * *